(12) United States Patent
Moses

(10) Patent No.: US 11,738,030 B2
(45) Date of Patent: Aug. 29, 2023

(54) TREATMENTS FOR DISTURBED CEREBRAL HOMEOSTASIS

(71) Applicant: Aneuryst, Inc., New York, NY (US)

(72) Inventor: Ziev B Moses, Boston, MA (US)

(73) Assignee: Aneuryst, Inc., New York, NY (US)

( * ) Notice: Subject to any disclaimer, the term of this patent is extended or adjusted under 35 U.S.C. 154(b) by 0 days.

(21) Appl. No.: 18/047,276

(22) Filed: Oct. 18, 2022

(65) Prior Publication Data

US 2023/0133200 A1    May 4, 2023

Related U.S. Application Data

(60) Provisional application No. 63/273,925, filed on Oct. 30, 2021.

(51) Int. Cl.
A61K 31/551 (2006.01)
A61P 25/28 (2006.01)

(52) U.S. Cl.
CPC ............ *A61K 31/551* (2013.01); *A61P 25/28* (2018.01)

(58) Field of Classification Search
CPC combination set(s) only.
See application file for complete search history.

(56) References Cited

U.S. PATENT DOCUMENTS

| | | |
|---|---|---|
| 2019/0298733 A1 | 10/2019 | Rosen et al. |
| 2021/0290635 A1 | 9/2021 | Rosen et al. |

OTHER PUBLICATIONS

NIMOTOP® (Product Monograph, nimodipine tablets Bayer Standard, 30 mg, Adjunct in the Management of Subarachnoid Hemorrhage, Nov. 2011, pp. 1-27).*
Christine Barry, Renee J Turner, Frances Corrigan, Robert Vink, New Therapeutic Approaches To Subarachnoid Hemorrhage, *Expert Opinion On Investigational Drugs* 21(6):845-59 (Apr. 2012).
Bonaventura A, et al. Update on Inflammatory Biomarkers and Treatments in Ischemic Stroke. *Int J Mol Sci.* 2016;17(12):1967.
Breitenlechner C, Gassel M, Hidaka H, et al. Protein kinase A in complex with Rho-kinase inhibitors Y-27632, Fasudil, and H-1152P: structural basis of selectivity. Structure (London, England : 1993). Dec. 2003;11(12):1595-1607.
Siu-Lung Chan and Marilyn J Cipolla, Treatment With Low Dose Fasudil For Acute Ischemic Stroke In Chronic Hypertension, *Journal of Cerebral Blood Flow & Metabolism* 2017, vol. 37(9) 3262-3270 (2017).
Chiba T and Umegaki K. Pivotal roles of monocytes/macrophages in stroke. *Mediators Inflamm.* 2013:2013:759103.
Disabato et al. "Neuroinflammation: the devil is in the details." *J Neurochem.* 2016;139 (Suppl 2):136-153.
Dong Y, Cao W, Cheng X, Fang K, Wu F, Yang L, Xie Y, Dong Q. Low-dose intravenous tissue plasminogen activator for acute ischaemic stroke: an alternative or a new standard? *Stroke Vasc Neurol.* Oct. 25, 2016;1(3):115-121.
Eide PK, Rapoport BI, Gormley WB, Madsen Jr. "A dynamic nonlinear relationship between the static and pulsatile components of intracranial pressure in patients with subarachnoid hemorrhage." *J Neurosurg.* 2010;112(3):616-625.
Fassbender K, Hodapp B, Rossol S, Bertsch T, Schmeck J, Schütt S, Fritzinger M, Horn P, Vajkoczy P, Kreisel S, Brunner J, Schmiedek P, Hennerici M. Inflammatory cytokines in subarachnoid haemorrhage: association with abnormal blood flow velocities in basal cerebral arteries. *J Neurol Neurosurg Psychiatry.* Apr. 2001;70(4):534-7.
Fujii M, Duris K, Altay O, Soejima Y, Sherchan P, Zhang JH. Inhibition of Rho kinase by hydroxyfasudil attenuates brain edema after subarachnoid hemorrhage in rats. *Neurochem Int.* Feb, 2012;60(3):327-33.
Hanafy KA, Grobelny B, Fernandez L, Kurtz P, Connolly ES, Mayer SA, Schindler C, Badjatia N. Brain interstitial fluid TNF-alpha after subarachnoid hemorrhage. *J Neurol Sci.* Apr. 15, 2010;291(1-2):69-73.
Höllig A, Remmel D, Stoffel-Wagner B, Schubert GA, Coburn M, Clusmann H. Association of early inflammatory parameters after subarachnoid hemorrhage with functional outcome: a prospective cohort study. *Clin Neurol Neurosurg.* Nov. 2015;138:177-83.
Wei Huang, Qianqian Lan, Li Jiang, Wenya Yan, Fen Tang, Chaolan Shen, Hui Huang, Haibin Zhong, Jian LV, Siming Zeng, Min Li, Zhongxiang MO, Bing Hu, Ning Liang, Qi Chen, Mingyuan Zhang, Fan Xu, Ling Cui, Fasudil Attenuates Glial Cell-Mediated Neuroinflammation Via Erk1/2 and Akt Signaling Pathways After Optic Nerve Crush, *Molecular Biology Reports* (2020) 47:8963-8973.
Qin Li, Xian-Ju Huang, Wei He, Jie Ding, Jun-Ting Jia, Gang Fu, Hong-Xing Wang, Lian-Jun Guo, Neuroprotective Potential of Fasudil Mesylate in Brain Ischemia-Reperfusion Injury of Rats, *Cell Mol Neurobiol* (2009) 29:169-180.
Liu Jianyu, Mu Zhihao, Wang Liping, Wen Ruoxue, Wang Yongting, Yang Guoyuan, Zhang Zhijun, Reduction of Brain Injury After Stroke in Hyperglycemic Rats Via Fasudil Pretreatment, *J. Shanghai Jiao Tong Univ. (Sci.)*, 2019, 24(6): 723-731.
Lochner A & Moolman JA. The many faces of H89: a review. *Cardiovasc Drug Rev.* 2006 Fall-Winter; 24(3-4):261-74.
Cedric Logé, Xavier Siomboing, Valérie Wallez, Elizabeth Scalbert, Caroline Bennejean, Christelle Cario-Tourmaniantz, Gervaise Loirand, Bernard Gressier, Pierre Pacaud & Michel Luyckx, Synthesis and Pharmacological Study of Rho-Kinase Inhibitors: Pharmacomodulations on the Lead Compound Fasudil, *Journal of Enzyme Inhibition and Medicinal Chemistry*, Apr. 2003;18(2):127-38.
Magni F, et al. High-Resolution Intracranial Pressure Burden and Outcome in Subarachnoid Hemorrhage. *Stroke.* 2015;46(9):2464-2469.
K.Y. Manjunath, Estimation of Cranial Volume in Dissecting Room Cadavers, *Journal of the Anatomical Society of India* vol. 51, No. 2 (Jul. 2002-Dec. 2002).

(Continued)

*Primary Examiner* — Kathrien A Hartsfield
(74) *Attorney, Agent, or Firm* — Mitchell M. Wong

(57) ABSTRACT

Disclosed herein are compounds and methods for the treatment of disturbances to cerebral homeostasis using isoquinoline derivatives and pharmaceutical compositions thereof.

10 Claims, 3 Drawing Sheets

(56) References Cited

OTHER PUBLICATIONS

Matsumae M, Kikinis R, Mórocz IA, Lorenzo AV, Sándor T, Albert MS, Black PM, Jolesz FA. Age-related changes in intracranial compartment volumes in normal adults assessed by magnetic resonance imaging. *J Neurosurg.* Jun. 1996;84(6):982-91.
Narumiya S, Ishizaki T, Uehata M. Use and properties of Rock-specific inhibitor Y-27632. *Methods Enzymol.* 2000;325:273-84.
Taku Nonaka, Tatsuya Ishikawa, Koji Yamaguchi, Takayuki Yasuda, Yoshihiro Omura, Mieko Oka, and Takakazu Kawamata, Intra-Arterial Injection of Fasudil Hydrochloride for Cerebral Vasospasm Secondary to Bacterial Meningitis, *NMC Case Report Journal* 2018; 5: 91-94.
Sarrafzadeh, A., Schlenk, F., Gericke, C. et al. Relevance of Cerebral Interleukin-6 After Aneurysmal Subarachnoid Hemorrhage. *Neurocrit Care* 13, 339-346 (2010).
Sato M, Tani E, Fujikawa H, Kaibuchi K. Involvement of Rho-kinase-mediated phosphorylation of myosin light chain in enhancement of cerebral vasospasm. *Circ Res.* Aug. 4, 2000;87(3):195-200.
Yoshio Suzuki, MD, Masato Shibuya, MD, Shin-ichi Satoh, PhD, Yuka Sugimoto, BS, Kintomo Takakura, MD, A Postmarketing Surveillance Study of Fasudil Treatment After Aneurysmal Subarachnoid Hemorrhage, *Surgical Neurology* 68 (2007) 126-132.
Kazuhiro Tanaka, M.D., et al., Treatment of Cerebral Vasospasm With Intraarterial Fasudil Hydrochloride, *Congress of Neurological Surgeons* (Feb. 2005).
Xin YL, Yu JZ, Yang XW, Liu CY, Li YH, Feng L, Chai Z, Yang WF, Wang Q, Jiang WJ, Zhang GX, Xiao BG, Ma CG. FSD-C10: A more promising novel ROCK inhibitor than Fasudil for treatment of CNS autoimmunity. *Biosci Rep.* Jul. 29, 2015;35(5):e00247.
Kentaro Yamashitaa, Yoshinori Kotania, Yoshimi Nakajima, Masamitsu Shimazawa, Shin-ichi Yoshimura, Shigeru Nakashima, Toru Iwama, Hideaki Hara, Fasudil, A Rho Kinase (Rock) Inhibitor, Protects Against Ischemic Neuronal Damage In Vitro and In Vivo by Acting Directly on Neurons, *Brain Research* 1154 (2007) 215-224.
Jizong Zhao et al., Efficacy and Safety of Fasudil in Patients With Subarachnoid Hemorrhage: Final Results of a Randomized Trial of Fasudil Versus Nimodipine, *Neurol Med Chir (Tokyo)* 51, 679-683, 2011.
Chen J, Yin W, Tu Y, Wang S, Yang X, Chen Q, Zhang X, Han Y, Pi R. L-F001, a novel multifunctional ROCK inhibitor, suppresses neuroinflammation in vitro and in vivo: Involvement of NF-κB inhibition and Nrf2 pathway activation. *Eur J Pharmacol.* Jul. 5, 2017;806:1-9.
Li L, Lou X, Zhang K, Yu F, Zhao Y, Jiang P. Hydrochloride fasudil attenuates brain injury in ICH rats. *Transl Neurosci.* Apr. 20, 2020; 11(1):75-86.
Satoh S, Ikegaki I, Suzuki Y, Asano T, Shibuya M, Hidaka H. Neuroprotective properties of a protein kinase inhibitor against ischaemia-induced neuronal damage in rats and gerbils. *Br J Pharmacol.* Aug. 1996;118(7):1592-6.
Zhao J, Zhou D, Guo J, Ren Z, Zhou L, Wang S, Xu B, Wang R. Effect of fasudil hydrochloride, a protein kinase inhibitor, on cerebral vasospasm and delayed cerebral ischemic symptoms after aneurysmal subarachnoid hemorrhage. *Neurol Med Chir (Tokyo).* Sep. 2006;46(9):421-8.

\* cited by examiner

TREATMENTS FOR DISTURBED CEREBRAL HOMEOSTASIS

CROSS-REFERENCE TO RELATED APPLICATIONS

This application claims priority to, and the benefit of, U.S. Provisional Patent Application No. 63/273,925, filed Oct. 30, 2021, which is incorporated herein by reference in its entirety.

FIELD OF THE INVENTION

The present invention relates to compositions, formulations, methods, and kits for treating disturbed cerebral homeostasis, including treatments comprising administration of an isoquinoline derivative.

BACKGROUND OF THE INVENTION

Cerebral homeostasis involves control of neuroinflammatory events in the central nervous system (CNS), maintenance of normal intracranial pressure and fluid balance, and regulation of brain metabolism.

CNS neuroinflammation is an inflammatory response within the brain or spinal cord. This inflammation is mediated by the production of cytokines, chemokines, reactive oxygen species, and secondary messengers. Although controlled neuroinflammatory processes serve a protective role, prolonged acute CNS neuroinflammation leads to exacerbation of brain injury and cell death. DiSabato et al. "Neuroinflammation: the devil is in the details." *J Neurochem.* 2016; 139 (Suppl 2):136-153.

Intracranial pressure ("ICP") is the pressure within the craniospinal compartment. Gomes & Bhardwaj, Chapter 4: Normal Intracranial Pressure Physiology, in *Cerebrospinal Fluid in Clinical Practice* (2009). Abnormal ICP—including elevated ICP (also known as "heightened ICP," "HICP," or "intracranial hypertension")—is a serious medical emergency associated with death and permanent neurological injuries and deficits (including motor and cognitive deficits).

Disturbances to cerebral homeostasis, and in particular disturbances in neuroinflammatory control or ICP/fluid maintenance can lead to permanent neurological deficits and death. There remains a need for compositions, formulations, kits, and methods for treating subjects with, or at risk of, disturbed cerebral homeostasis.

BRIEF SUMMARY OF THE INVENTION

A method of treating a patient experiencing or at risk of disturbed cerebral homeostasis, comprising administering to the patient an isoquinoline derivative that regulates vascular activity by modulating rho-associated coiled-coil containing kinase (ROCK) activity.

At least one embodiment provides a method of treating a patient experiencing or at risk of disturbed cerebral homeostasis, comprising administering to the patient a pharmaceutical formulation of an isoquinoline derivative that regulates vascular activity by modulating rho-associated coiled-coil containing kinase activity, and detecting at 90 days an improvement in neurological outcome caused by or attributed to said disturbed cerebral homeostasis.

At least one embodiment provides a method of treating a patient experiencing or at risk of disturbed cerebral homeostasis, wherein said disturbed cerebral homeostasis comprises acute CNS neuroinflammation, said method comprising administering to said patient an isoquinoline derivative that regulates vascular activity by modulating rho-associated coiled-coil containing kinase activity in an amount that is effective to produce at 90 days an improvement in neurological outcome.

At least one embodiment provides a method of treating a patient experiencing or at risk of disturbed cerebral homeostasis, wherein said disturbed cerebral homeostasis comprises abnormal ICP, wherein said patient is intolerant or determined to be intolerant of enteric nimodipine, wherein said method comprises parenterally administering to said patient a therapeutic amount of an isoquinoline derivative that regulates vascular activity by modulating rho-associated coiled-coil containing kinase activity in an amount that is effective to produce at 90 days an improvement in neurological outcome.

At least one embodiment provides a method of treating a patient experiencing or at risk of disturbed cerebral homeostasis, wherein said disturbed cerebral homeostasis comprises hydrocephalus, wherein said patient is intolerant or determined to be intolerant of enteric nimodipine, wherein said method comprises parenterally administering to said patient a therapeutic amount of an isoquinoline derivative that regulates vascular activity by modulating rho-associated coiled-coil containing kinase activity in an amount that is effective to produce at 90 days an improvement in neurological outcome.

At least one embodiment provides a method of treating a patient experiencing or at risk of disturbed cerebral homeostasis, wherein said disturbed cerebral homeostasis follows meningitis, said method comprising parenterally administering to said patient a therapeutic amount of an isoquinoline derivative that regulates vascular activity by modulating rho-associated coiled-coil containing kinase activity in an amount that is effective to produce at 90 days an improvement in neurological outcome.

At least one embodiment provides a method of treating a patient experiencing or at risk of disturbed cerebral homeostasis, wherein said disturbed cerebral homeostasis follows a brain injury that deposits blood in the subarachnoid space, said method comprising parenterally administering to said patient a therapeutic amount of an isoquinoline derivative that regulates vascular activity by modulating rho-associated coiled-coil containing kinase activity in an amount that is effective to produce at 90 days an improvement in neurological outcome.

At least one embodiment provides a method of treating a patient experiencing or at risk of disturbed cerebral homeostasis, wherein said disturbed cerebral homeostasis follows meningitis or a brain injury that deposits blood in the subarachnoid space, said method comprising parenterally administering to said patient a therapeutic amount of fasudil, or a pharmaceutically acceptable salt thereof, in an amount that is effective to produce at 90 days an improvement in neurological outcome.

At least one embodiment provides a method of treating a patient experiencing or at risk of disturbed cerebral homeostasis, wherein said disturbed cerebral homeostasis follows meningitis or a brain injury that deposits blood in the subarachnoid space, said method comprising parenterally administering to said patient a therapeutic amount of hydroxyfasudil, or a pharmaceutically acceptable salt thereof, in an amount that is effective to produce at 90 days an improvement in neurological outcome.

At least one embodiment provides a method of treating a patient experiencing or at risk of disturbed cerebral homeostasis, wherein said disturbed cerebral homeostasis follows meningitis or a brain injury that deposits blood in the subarachnoid space, said method comprising administering to said patient fasudil hydrochloride or hydroxyfasudil hydrochloride, or a pharmaceutically acceptable salt thereof, in an amount that is effective to produce at 90 days an improvement in the Lawton Instrumental Activities of Daily Living Scale score.

At least one embodiment provides a method of treating a patient experiencing or at risk of disturbed cerebral homeostasis, wherein said disturbed cerebral homeostasis follows meningitis or a brain injury that deposits blood in the subarachnoid space, and wherein said patient is intolerant or determined to be intolerant of enteric nimodipine, said method comprising: parenterally administering to said patient 30 mg of fasudil hydrochloride or hydroxyfasudil hydrochloride, and detecting at 90 days an improvement in the Lawton Instrumental Activities of Daily Living Scale score.

At least one embodiment provides a method of treating a patient at risk of disturbed cerebral homeostasis, comprising parenterally administering to said patient a therapeutic amount of an isoquinoline derivative, or a pharmaceutically acceptable salt thereof.

At least one embodiment provides a method of treating a patient at risk of disturbed cerebral homeostasis, comprising parenterally administering to said patient a therapeutic amount of an isoquinoline derivative, or a pharmaceutically acceptable salt thereof, wherein said therapeutic amount is effective to prevent neurological deficits or improve neurological outcome.

At least one embodiment provides a method of treating a patient at risk of disturbed cerebral homeostasis, comprising parenterally administering to said patient a therapeutic amount of an isoquinoline derivative, or a pharmaceutically acceptable salt thereof, wherein said therapeutic amount is effective to reduce the incidence or severity of ischemic deficits.

A method of treating a patient at risk of acute CNS neuroinflammation, comprising parenterally administering to said patient a therapeutic amount of an isoquinoline derivative, or a pharmaceutically acceptable salt thereof, wherein said therapeutic amount is effective to prevent neurological deficits or to improve neurological outcome or to reduce the incidence or severity of ischemic deficits.

At least one embodiment provides a method of treating a patient experiencing acute CNS neuroinflammation, comprising parenterally administering to said patient a therapeutic amount of an isoquinoline derivative, or a pharmaceutically acceptable salt thereof, wherein said therapeutic amount is effective to prevent neurological deficits or to improve neurological outcome or to reduce the incidence or severity of ischemic deficits.

At least one embodiment provides a method of treating a patient at risk of abnormal ICP, comprising parenterally administering to said patient a therapeutic amount of an isoquinoline derivative, or a pharmaceutically acceptable salt thereof, wherein said therapeutic amount is effective to prevent neurological deficits or to improve neurological outcome or to reduce the incidence or severity of ischemic deficits.

At least one embodiment provides a method of treating a patient experiencing abnormal ICP, comprising parenterally administering to said patient a therapeutic amount of an isoquinoline derivative, or a pharmaceutically acceptable salt thereof, wherein said therapeutic amount is effective to prevent neurological deficits or to improve neurological outcome or to reduce the incidence or severity of ischemic deficits.

At least one embodiment provides a method of treating a patient at risk of disturbed cerebral homeostasis, wherein said patient further has meningitis, comprising parenterally administering to said patient a therapeutic amount of an isoquinoline derivative, or a pharmaceutically acceptable salt thereof, wherein said therapeutic amount is effective to prevent neurological deficits or to improve neurological outcome or to reduce the incidence or severity of ischemic deficits.

At least one embodiment provides a method of treating a patient at risk of disturbed cerebral homeostasis, wherein said patient further has suffered a brain injury that deposits blood in the subarachnoid space, comprising parenterally administering to said patient a therapeutic amount of an isoquinoline derivative, or a pharmaceutically acceptable salt thereof, wherein said therapeutic amount is effective either to prevent neurological deficits or to improve neurological outcome or to reduce the incidence or severity of ischemic deficits.

At least one embodiment provides a method of treating a patient at risk of disturbed cerebral homeostasis, wherein said patient either has meningitis or has suffered a brain injury that deposits blood in the subarachnoid space, comprising parenterally administering to said patient a therapeutic amount of fasudil, or a pharmaceutically acceptable salt thereof, wherein said therapeutic amount is effective to prevent neurological deficits or to improve neurological outcome or to reduce the incidence or severity of ischemic deficits.

At least one embodiment provides a method of treating a patient at risk of disturbed cerebral homeostasis, wherein said patient either has meningitis or has suffered a brain injury that deposits blood in the subarachnoid space, comprising parenterally administering to said patient a therapeutic amount of hydroxyfasudil, or a pharmaceutically acceptable salt thereof, wherein said therapeutic amount is effective to prevent neurological deficits or to improve neurological outcome or to reduce the incidence or severity of ischemic deficits.

At least one embodiment provides a method of treating a patient at risk of disturbed cerebral homeostasis, wherein said patient either has meningitis or has suffered a brain injury that deposits blood in the subarachnoid space, comprising parenterally administering to said patient a therapeutic amount of fasudil hydrochloride or hydroxyfasudil hydrochloride.

At least one embodiment provides a method of treating a patient at risk of disturbed cerebral homeostasis, wherein said patient either has meningitis or has suffered a brain injury that deposits blood in the subarachnoid space, comprising parenterally administering to said patient 30 mg of fasudil hydrochloride or hydroxyfasudil hydrochloride.

The foregoing embodiments refer to methods of treating a patient. Also provided within the scope of the invention are the foregoing compounds, compositions and substances described in the above embodiments, for use in the prevention or treatment of the foregoing disease or condition, where the foregoing compounds, compositions and substances are administered to a patient in need thereof. For example, in line with the embodiment described above at the first paragraph in the "Brief Summary of the Invention" section, there is also provided an isoquinoline derivative for use in the treatment or prevention of disturbed cerebral homeostasis, wherein the isoquinoline derivative regulates vascular activity by modulating rho-associated coiled-coil containing kinase (ROCK) activity.

Also provided within the scope of the invention is the use of the foregoing compounds, compositions and substances described in the above embodiments in the manufacture of a medicament for the treatment or prevention of the foregoing disease or condition, where the foregoing compounds, compositions and substances are administered to a patient in need thereof. For example, in line with the embodiment described above at the first paragraph in the "Brief Summary of the Invention" section, there is also provided the use of an isoquinoline derivative in the manufacture of a medicament for the treatment or prevention of disturbed cerebral homeostasis, wherein the isoquinoline derivative regulates vascular activity by modulating rho-associated coiled-coil containing kinase (ROCK) activity.

INCORPORATION BY REFERENCE

Figure 1:
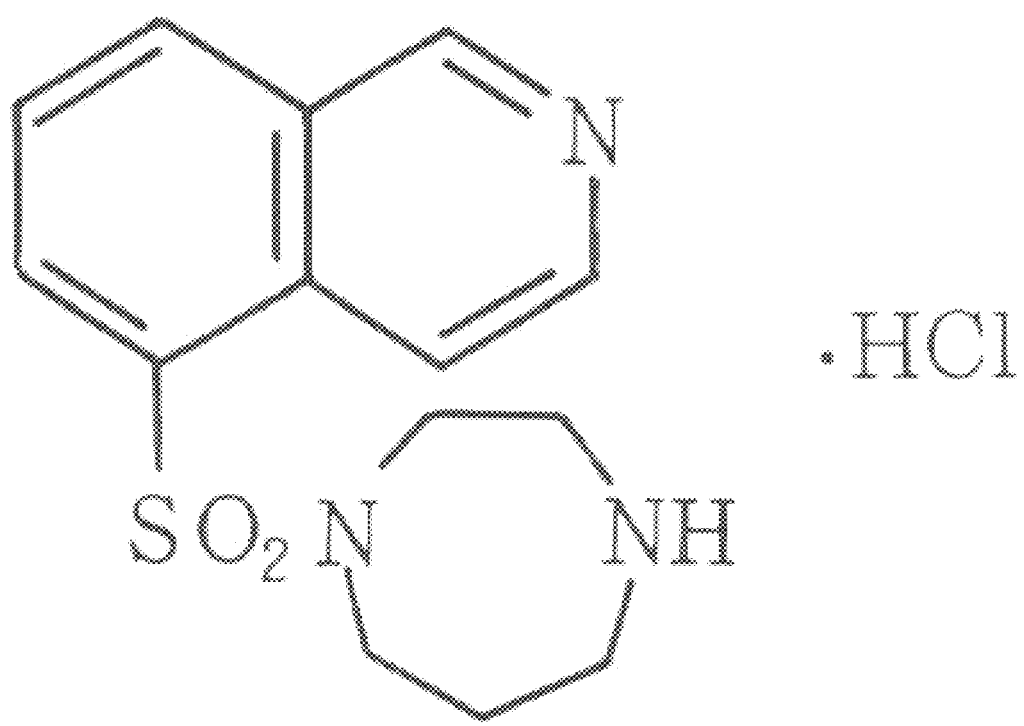
FIG. 1 is an illustration of the structural formula for fasudil hydrochloride.

References and citations to other documents, such as patents, patent applications, patent publications, journals, books, papers, and web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

DEFINITIONS

As used herein, unless specifically stated or obvious from context, the singular forms "a", "an" and "the" include plural referents unless the context clearly dictates otherwise. For example, reference to a "polypeptide" means one or more polypeptides.

As used herein, unless specifically stated or obvious from context, the term "abnormal ICP" includes any one or any combination of one or more of the following: a mean ICP above 5 mmHg in adults, a mean ICP above 3 mmHg in children, a mean ICP above 1.5 mmHg in infants, a "rounded" ICP waveform, an ICP waveform greater than 4 mmHg in amplitude, an ICP waveform more than 30% of the mean ICP, an ICP waveform in which P2 is greater than P1, large-amplitude ICP waveform peaks (dP), shortened ICP waveform rise times (dT), increased ICP rise time coefficients (dP/dT), Lundberg A waves, Lundberg B waves, a pulsatile ICP greater than 5 mmHg, or a $PTD_{ICP30}$ greater than 1.

As used herein, unless specifically stated or obvious from context, the term "about" refers to a number or range of numbers is understood to mean the stated number and numbers+/−10% thereof, or 10% below the lower listed limit and 10% above the higher listed limit for the values listed for a range.

As used herein, unless specifically stated or obvious from context, the term "administer" means to give or to apply. The term "administering" as used herein includes in vivo administration, as well as administration directly to tissue ex vivo. Generally, compositions may be administered systemically either orally, buccally, parenterally, topically, by inhalation or insufflation (i.e., through the mouth or through the nose), administered rectally in dosage unit formulations containing conventional nontoxic pharmaceutically acceptable carriers, adjuvants, and vehicles as desired, or administered locally by means such as, but not limited to, injection, implantation, grafting, topical application, or parenterally.

As used herein, unless specifically stated or obvious from context, the term "and/or" means "and" or "or."

As used herein, unless specifically stated or obvious from context, the term "angiogram-negative SAH" refers to a SAH that does not show an aneurysm by 4-vessel catheter angiography.

As used herein, unless specifically stated or obvious from context, the term "derivative" is a broad term, and is to be given its ordinary and customary meaning to a person of ordinary skill in the art (and is not to be limited to a special or customized meaning), and refers without limitation to any compound as described herein incorporating one or more derivative groups, or being substituted by or functionalized to include one or more derivative groups. Derivatives include but are not limited to esters, amides, anhydrides, acid halides, thioesters, phosphates, triphosphates, and β-sulfenyl derivatives.

As used herein, unless specifically stated or obvious from context, the term "diluent" is a broad term, and is to be given its ordinary and customary meaning to a person of ordinary skill in the art (and is not to be limited to a special or customized meaning), and refers without limitation to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood, Ringer's lactate, Ringer's acetate, plasmalyte or 0.9% saline.

As used herein, the term "disturbed cerebral homeostasis" can refer to any one or combination of the following: acute CNS neuroinflammation; abnormal intracranial pressure; abnormal cerebral perfusion pressure; abnormal brain-tissue oxygen pressure; pathological values for parameters derived from cerebral microdialysis; or a state of being at risk of having any one or more of the foregoing.

As used herein, unless specifically stated or obvious from context, the term "effective amount" refers to the amount necessary or sufficient to realize a desired biologic effect.

As used herein, unless specifically stated or obvious from context, the term "functional outcome" shall include any one or combination of the following: the conventional Glasgow outcome score (GOS); the extended Glasgow outcome score (GOSE); the Rankin Stroke Outcome Scale; the modified Rankin Score; the NIH Stroke Scale/Score; the Barthel Index; the Disability Rating Scale; the Karnofsky Performance Status scale; the Lawton Instrumental Activities of Daily Living Scale; the Mini-Mental State Examination (MMSE); the Montreal cognitive assessment; neurocognitive assessment; Prognosis on Admission of Aneurysmal Subarachnoid Hemorrhage Grading Scale (PAASH); the Rankin Disability Index (RDI); the Richmond Agitation-Sedation Scale (RASS); the modified Tardieu Scale (mTS); time to discharge to home; World Federation of Neurological Surgeons Grading Scale for Subarachnoid Hemorrhage (WFNS), or other measure of patient capacity, dysfunction, disability, or handicap (including dichotomized versions of any of the foregoing).

As used herein, unless specifically stated or obvious from context, the term "infarction" refers to an insufficiency of arterial or venous blood supply due to emboli, thrombi, mechanical factors, or pressure that produces a macroscopic area of necrosis. The term "cerebral infarction" as used herein refers to a loss of brain tissue subsequent to the transient or permanent loss of circulation and/or oxygen delivery to the cerebrum. The term "infarct" as used herein refers to an area of necrosis resulting from a sudden insufficiency of arterial or venous blood supply.

As used herein, unless specifically stated or obvious from context, the term "inflammation" refers to the physiologic process by which vascularized tissues respond to injury. See, e.g., *Fundamental Immunology*, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses. The term "subacute inflammation" as used herein refers to a tissue reaction typically seen subsequent to the early inflammatory process characterized by a mixture of neutrophils, lymphocytes, and occasionally macrophages and/or plasma cells.

As used herein, unless specifically stated or obvious from context, the term "ischemia" refers to a lack of blood supply and oxygen that occurs when reduced perfusion pressure distal to an abnormal narrowing (stenosis) of a blood vessel is not compensated by autoregulatory dilation of the resistance vessels. As used herein, unless specifically stated or obvious from context, the term "cortical spreading ischemia" refers to a condition characterized by diagnostic markers that include, but are not limited to, the presence of blood in the CSF and/or a recent history of a SAH and/or development of neurological deterioration one to 14 days after SAH when the neurological deterioration is not due to another cause that can be diagnosed, including but not limited to seizures, hydrocephalus, increased intracranial pressure, infection, intracranial hemorrhage or other systemic factors and detection of propagating waves of depolarization with vasoconstriction detected by electrocorticography. Cortical spreading ischemia-associated symptoms include, but are not limited to, paralysis on one side of the body, inability to vocalize the words or to understand spoken or written words, and inability to perform tasks requiring spatial analysis. Such symptoms may develop over a few days, or they may fluctuate in their appearance, or they may present abruptly.

As used herein, unless specifically stated or obvious from context, the term "parenteral" refers to introduction into the body by way of an injection (i.e., administration by injection) outside the gastrointestinal tract, including, for example, subcutaneously (i.e., an injection beneath the skin), intramuscularly (i.e., an injection into a muscle); intravenously (i.e., an injection into a vein), intrathecally (i.e., an injection into the subarachnoid space of the spine), intracisternally, intraventricularly, or by infusion techniques. A parenterally administered composition is delivered using a needle, e.g., a surgical needle. The term "surgical needle" as used herein, refers to any needle adapted for delivery of fluid (i.e., matter capable of flow) compositions into a selected anatomical structure. Injectable preparations, such as sterile injectable aqueous or oleaginous suspensions, may be formulated according to the known art using suitable dispersing or wetting agents and suspending agents.

As used herein, unless specifically stated or obvious from context, the term "perimesencephalic SAH" refers to a subgroup of angiogram-negative SAH characterized by bleeding around the mesencephalon.

As used herein, unless specifically stated or obvious from context, the term "prodrug" refers to a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam)). A discussion of prodrugs is provided in Higuchi, T., et al., "Prodrugs as Novel Delivery Systems," *A. C. S. Symposium Series*, Vol. 14, and in *Bioreversible Carriers in Drug Design*, (Edward B. Roche, ed. 1987). The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

As used herein, unless specifically stated or obvious from context, the term "reduce" or "reducing" as used herein refers to a diminution, a decrease, an attenuation, limitation or abatement of the degree, intensity, extent, size, amount, density, number or occurrence of disorder in individuals at risk of developing the disorder.

As used herein, unless specifically stated or obvious from context, the terms "subject" or "individual" or "patient" are used interchangeably to refer to any living organism, including humans and animals.

As used herein, unless specifically stated or obvious from context, a subject "at risk of" a condition refers to a subject who has a higher risk of developing that condition than a control population. The control population may include, but is not limited to, one or more individuals selected at random from the general population (e.g., matched by age, gender, race and/or ethnicity) who have not been diagnosed or have a family history of the disorder. A subject can be considered at risk for a disorder if a "risk factor" associated with that disorder is found to be associated with that subject or if the subject has one or more predisposing factors to the development of the disorder. A risk factor can include any activity, trait, event or property associated with a given disorder, for example, through statistical or epidemiological studies on a population of subjects. A subject can thus be classified as being at risk for a disorder even if studies identifying the underlying risk factors did not include the subject specifically.

As used herein, unless specifically stated or obvious from context, the term "syndrome" refers to a pattern of symptoms indicative of some disease or condition.

As used herein, unless specifically stated or obvious from context, the term "treat" or "treating" includes abrogating, substantially inhibiting, slowing or reversing the progression of a disease, condition or disorder; substantially ameliorating clinical or esthetical symptoms of a condition; substantially preventing the appearance of clinical or esthetical symptoms of a disease, condition, or disorder; and/or protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

As used herein, unless specifically stated or obvious from context, the terms "Y-27632," "Y 32885," "GSK269962A," "SB772077B," "SR-715," "SR-899," "SLx-2119," and "Y-39983" refer to the respective compounds as defined on the PubChem database of the NIH National Library of Medicine https://pubchem.ncbi.nlm.nih.gov (Oct. 31, 2020).

DETAILED DESCRIPTION OF THE INVENTION

1. Cerebral Homeostasis

Cerebral homeostasis involves control of neuroinflammatory events in the central nervous system and maintenance of normal intracranial pressure. Orsini et al., "Versatility of the complement system in neuroinflammation, neurodegeneration and brain homeostasis," *Frontiers in Cellular Neuroscience; Lausanne* (Nov. 7, 2014).

Acute focal or total cerebral anoxic-ischemic, traumatic, inflammatory, metabolic, hemorrhagic, or neoplastic insults may result in coma, cerebral edema, total or regional cerebral blood flow (CBF) disturbances, and permanent cerebral metabolic derangements. Various insults to other organ systems may also ultimately jeopardize cerebral functioning. The initial insult is often followed by secondary (postresuscitative) cerebral changes that can be either ameliorated or prevented. Peter Safar, "Brain Monitoring and Homeostasis in Comatose, Critically Ill Patients," in *Critical Care Medicine Manual* (Weil & Daluz, eds., 1978).

Causal mechanisms for disturbed cerebral homeostasis remain obscure. Disturbed cerebral homeostasis can be idiopathic and/or associated with other disorders.

Intracranial disorders associated with disturbed cerebral homeostasis can include: abnormal activity in α-blocker substrates; abscess; benign intracranial hypertension; a brain injury (either traumatic, non-traumatic or both) that deposits blood in the subarachnoid space; brain tumors; choroid plexus tumor; contusions; depression fractures over major venous sinuses causing obstruction; diffuse traumatic brain/head injury; disturbances with CSF dynamics; early brain injury before onset of vasospasm; encephalitis; epileptic seizures; expansion of hematomas; focal edema secondary to trauma; global cerebral edema; heart failure; hydrocephalus (including communicating hydrocephalus, obstructive hydrocephalus, normal-pressure hydrocephalus, hydrocephalus ex-vacuo, and secondary hydrocephalus); infarction; intracerebral hemorrhage; intracranial hemorrhage; intraventricular hemorrhage; intraparenchymal hemorrhage; lead encephalopathy; metabolic/hypertensive encephalopathy; meningeal infiltration; meningitis; near drowning; neuroinflammation; Reye's syndrome; rupture of a saccular or fusiform cerebral aneurysm; spinal cord injury; subarachnoid hemorrhage (including aneurysmal subarachnoid hemorrhage or other non-traumatic subarachnoid hemorrhages); subdural hematoma; traumatic brain injury, traumatic hematomas (extradural, subdural, intracerebral), tumors or neoplasms (e.g., glioma, meningioma, metastasis); venous sinus thrombosis/cerebral venous thrombosis; and water intoxication. Additionally, the use of vasodilators (e.g., papaverine, hydralazine, nitroprusside) has been observed to elevate ICP. Extracranial disorders associated with ICP include raised intrathoracic pressure (e.g., from neurogenic pulmonary edema), central fever, severe hyponatremia, overcorrection of hypernatremia.

As used herein to describe the relationships between conditions or events, and unless otherwise specified, the term "associated" refers to temporal proximity without any necessary causal or ordinal relationship; one condition can be associated with another by occurring before, after, or contemporaneously with, the other.

2. CNS Neuroinflammation

CNS neuroinflammation can be divided into two categories: "acute" and "chronic." Chronic CNS neuroinflammation is also referred to as "degenerative" neuroinflammation.

Acute neuroinflammation refers to neuroinflammatory conditions of rapid onset, commonly as an immediate reaction to brain injury. In contrast, chronic neuroinflammation refers to inflammatory processes underlying gradual degenerative conditions such as Alzheimer's disease, amyotrophic lateral sclerosis, Friedreich's ataxia, Huntington's disease, Lewy body dementia, Machado-Joseph disease, multiple sclerosis, muscular dystrophy, Parkinson's disease, and spinal muscular atrophy.

Cerebral ischemia elicits an unrestrained inflammation, which is a complex phenomenon characterized by the production and interplay of cytokines, chemokines, adhesion molecules, free radicals, and destructive enzymes such as cyclo-oxygenase-2 (COX-2), inducible nitric oxide synthase (iNOS), and proteinases. In addition to circulating neutrophils and monocytes/macrophages, resident microglia, astrocytes, endothelial cells and neurons are also involved in in situ inflammatory reactions.

A. Cellular Participation in CNS Neuroinflammation (1) Role of Leukocytes Generally Following ischemia, leukocytes can induce damage by several mechanisms. First, leukocytes may physically obstruct vascular capillaries, causing reduced local tissue perfusion. Second, monocytes and polymorphonuclear leukocytes (PMNLs) exhibit clot-promoting prothrombotic activity in vitro. Third, leukocytes promote injury through the production of free radicals and other toxic compounds such as hypochlorous acid and various harmful enzymes.

Activated PMNLs enhance ischemic damage mainly through three mechanisms: reactive oxygen species (ROS) and protease production; cytokine-mediated enhanced inflammation; and complement activation.

(2) Role of Neutrophils

Neutrophils are among the first leukocytes to arrive in response to brain injury. Neutrophils were seen to be significantly increased at 3 days after ischemia. In vitro studies indicate that neutrophil accumulation and migration into the brain are promoted by macrophages, which produce inflammatory cytokines and upregulate adhesion molecules in endothelial cells.

During the acute phase of reperfusion in experimental and human specimens, polymorphonuclear neutrophils (PMNs) are not found in the ischemic parenchyma, but remain in the neurovascular unit (NVU) and in the leptomeningeal spaces. Here, they are attracted by accumulated signals released by ischemic brain in the interstitial fluid and then drained through perivascular spaces of cortical arterioles toward leptomeninges.

In vitro, ischemia alone was not able to induce PMN migration through the blood-brain barrier (BBB). Only after prolonged ischemia (12 h) were PMNs detected in cortical infarcted parenchyma. PMN accumulation in the damaged tissue correlates with stroke severity and worse stroke outcome.

The role of neutrophils in ischemic damage includes neutrophil production of free radicals via activation of NADPH oxidase; infarction volume is halved in transgenic mice lacking NADPH oxidase, indicating the contribution of NADPH oxidase in ischemic damage from neutrophils. Another free-radical-producing agent in neutrophils is iNOS, an enzyme producing high concentrations of reactive nitric oxide, which is associated with damage to cellular macromolecules.

Several studies tried to improve stroke outcomes by blocking PMN activation and recruitment, reducing their adhesion to endothelial cells or blocking mediators of BBB damage. The complex relationship between PMNs, ischemic stroke, reperfusion injury, and the augmented infective risk following anti-neutrophil treatment explain the high rate of treatment failure and discrepancies hanging over these attempts.

(3) Role of Microglia

Activated microglia play diversified roles in the evolution of ischemic damage. First, microglia can act as phagocytes, which involves direct cell-cell contact. Second, both human autopsy material and experimental animal models show that activated microglia produce proinflammatory cytokines such as IL-1β and TNF-α; additionally, IL-6 is induced in activated microglia in penumbra. Third, a variety of destructive enzymes—such as iNOS, NADPH oxidase, cPLA$_2$ and COX-2—are induced in microglial cells following ischemia. Finally, there is mounting evidence that microglia are capable of producing various neurotoxins such as quinolinic acid and excitotoxic levels of glutamate.

Within minutes of the onset of ischemia, microglial cells induce production of inflammatory cytokines, including IL-1β and TNF-α, which exacerbate tissue damage.

Soon after the onset of ischemic stroke, microglia (including brain resident macrophages) are activated and enhance circulating monocyte recruitment by releasing pro-inflammatory mediators, such as tumor necrosis factor (TNF-α), nitric oxide (NO), and superoxide.

B. Cytokine Participation in Neuroinflammation

Inflammatory cytokines, such as IL-1β, IL-6, and TNF-α are secreted by activated microglial cells and macrophages in stroke lesions and induce the expression of chemokines, which recruit more circulating monocytes/macrophages into lesions and lead to further brain damage.

Tumor necrosis factor-α and IL-1β are two pro-inflammatory cytokines, which play a very significant role in stroke. IL-1β and TNF-α also interact with each other and influence a series of signal transduction pathways, including the activation of COX-2, iNOS, and MMP-9.

Many studies demonstrated that cytokine-mediated effects on ischemic area are strictly related to a huge increase of their levels, considering that infarcts reach their final volume many hours before cytokines peak.

Cytokines provide important measures and predictors of neurological outcome following inflammatory events.

(1) TNF-α

TNF-α is a type II transmembrane protein bound to the membrane in a trimeric form.

TNF-α owns a dual role: it can both exacerbate and reduce infarct evolution. TNF-blocking with specific monoclonal antibodies confers neuroprotection. On the other hand, TNF-α produced by microglial cells was protective on ischemic neurons.

TNF-α can be cleaved by tumor necrosis factor-alpha converting enzyme (TACE) to generate a soluble molecule and acts through binding to two receptors—TNFR1 and TNFR2.

TNFR1 can stimulate apoptotic and necroptotic cell death, and thus, by acting through TNFR1, TNF-α itself indirectly stimulates apoptotic and necroptotic cell death.

After an intracerebral hemorrhage, TNF-α could predispose the brain to subsequent damage by causing a pro-adhesive state of the capillary endothelium, possibly via upregulation of adhesion molecules. TNF-α also increases blood-brain-barrier (BBB) permeability; causes pial artery constriction, stimulates astrocyte proliferation; has a direct toxic effect on the capillaries and oligodendrocytes; and is involved in demyelination and gliosis in brain injury. Furthermore, TNF-α activates the endothelium for leukocyte adherence; promotes procoagulation activity by increasing the levels of tissue factor, von Willebrand factor, and platelet-activating factor (PAF); stimulates expression of leukocyte-endothelial adhesion molecules; activates neutrophil free-radical release; and causes mitochondrial free-radical production and apoptosis.

In the CSF taken from normal adults (i.e., adults who initially were suspected, but then subsequently were excluded diagnostically, from hemorrhage or meningitis), the CSF concentration of TNF-α was 0.18 (SEM 0.16) pg/mL. In contrast, under inflammatory conditions (e.g., on Day 5 after an aneurysmal rupture), TNF-α was observed to be 3.62 (SEM 0.50) pg/mL. Fassbender et al. *J Neurol Neurosurg Psychiatry.* 2001 April; 70(4):534-7.

In brain interstitial fluid, a study which collected 91 measurements of TNF-α from 14 patients over 3 days (SAH days 4-6) reported a median concentration of 753.1 pg/mL, with an intraquartile range of 372.1-1100.5 pg/mL. Hanafy et al. *J Neurol Sci.* 2010 Apr. 15; 291(1-2):69-73.

Increased serum and cerebrospinal fluid levels of TNF-α after stroke correlate with infarct volume and severity of neurological impairment.

In cases of ischemic stroke, the peak of TNF-α in CSF at 24 h after ictus correlated with clinical outcomes.

Although anti-TNF-α strategies have proved beneficial in other clinical settings such as inflammatory bowel disease, there are no clinical trials of anti-TNF-α agents in stroke.

(2) Interleukin-1β:

IL-1β is a pro-inflammatory cytokine that signals through the IL-1 receptor type I, which can be competitively blocked by the receptor antagonist (IL-1Ra).

IL-1β is released by different compartments of the NVU, and produced as a precursor protein (pro-IL-1β) which requires cleavage by ICE (caspase-1) to become biologically active.

The CSF concentration of IL-1β in normal adults was 0.00 (SEM 0.00) pg/mL, but was seen to increase to 5.78 (SEM 0.83) pg/mL under inflammatory conditions. Fassbender et al ibid.

Exogenous administration of IL-1β has been seen to exacerbate ischemic brain injury. IL-1β can stimulate astrocyte proliferation and cerebral edema, induce leukocyte infiltration, and increase de novo synthesis of endothelial adhesion molecules ICAM-1 and ELAM.

In ischemic stroke, IL-1β levels were increased in CSF after 6 h, but did not correlate with infarct size or clinical outcome. However, there are no human studies investigating outcome and IL-1β in SAH.

(3) IL-6

IL-6 is one of the major brain cytokines primarily produced by astrocytes and microglia.

The function of IL-6 is complex and ambivalent: neuroprotective as well as neuroinflammatory effects arise from IL-6. IL-6 and chemokines such as IL-8, monocyte chemoattractant protein-1 (MCP-1), RANTES (regulated on activation, normal T expressed and secreted), and γ-interferon-inducible protein-10 (IP-10) are increased in ischemia and involved in inflammation, gliosis and leukocyte activation and adhesion.

Increase of IL-6 expression has been detected in the context of multiple neurological diseases associated with CNS injury or inflammation. The CSF concentration of IL-6 in normal adults was observed to be 0.0004 (SEM 0.0001) ng/mL, but was seen to increase over 10,000-fold to 9.15 (SEM 2.26) ng/mL under inflammatory conditions. Fassbender et al ibid.

In another study, the median CSF IL-6 concentration recorded by bedside microdialysis in 38 aSAH patients over 10 days was observed to be 3563.9 pg/ml, with an intraquartile range of 374.2-21,321.0 pg/ml. Sarrafzadeh et al, *Neurocrit Care* (2010) 13:339-346.

The median concentration of IL-6 in cerebral extracellular fluid (ECF) was reported to be 437.3 pg/ml, with an intraquartile range of 49.5-4722.7 pg/ml. Cerebral, but not plasma IL-6, levels were indicative of the development of DCI in symptomatic patients (ECF p=0.003; CSF p=0.001). Increased CSF IL-6 levels were significantly associated with poor outcome.

IL-6 is one of the first cytokines primarily found to be elevated in CSF after aSAH. Elevated serum IL-6 levels are related with unfavorable outcome after aSAH, but only at discharge. However, a significant relationship could not be established between serum IL-6 levels and outcome six months after aSAH, though this may have been due to the high 27% drop-out rate. Höllig et al, *Clin. Neurol. Neurosurg.* 2015; 138:177-183.

Detailed information concerning these neuroinflammatory mechanisms can be found in Bonaventura A, et al. Update on Inflammatory Biomarkers and Treatments in Ischemic Stroke. *Int Mol Sci.* 2016; 17(12):1967; Chiba T, et al. "Pivotal roles of monocytes/macrophages in stroke." *Mediators Inflamm.* 2013:759103; Höllig A, et al. "Association of early inflammatory parameters after subarachnoid hemorrhage with functional outcome: A prospective cohort study." *Clin Neurol Neurosurg.* 2015; 138:177-183; Jari Koistinaho and Juha Yrjänheikki, "Inflammation and Potential Anti-Inflammatory Approaches in Stroke," from *Neuroinflammation, 2nd Edition: Mechanisms and Management* (P. L. Wood ed. 2003); Sarrafzadeh A, et al. "Relevance of cerebral interleukin-6 after aneurysmal subarachnoid hemorrhage." *Neurocrit Care.* 2010; 13(3):339-346.

C. Current Neuroinflammation Treatments and Shortcomings

Current treatment options for neuroinflammation include statins, thiazolidinediones, and anti-inflammatory agents. However, significant drawbacks persist with each of these options, including increased risks of stroke, heart failure, bleeding and all-cause mortality.

2. Intracranial Pressure

A. Intracranial Pressure (Generally)

Intracranial pressure (ICP) is defined as the pressure within the craniospinal compartment.

A variety of methods for monitoring ICP is known to those of ordinary skill in treating patients with abnormal ICP. One example of such a method is the use of a pressure transducer (such as an external strain gauge) connected to an extraventricular drain such that the pressure transducer is in line with the interventricular foramina (foramen of Monro). This example is illustrative only and not intended to act as a comprehensive listing of the methods for monitoring ICP.

B. Munro-Kellie Hypothesis

ICP is assessed under the Munro-Kellie hypothesis, which proposes that in individuals whose fontanelles have fused, the sum of volumes of brain, cerebrospinal fluid (CSF), and intracranial blood is constant.

Under normal conditions, an increase in the volume of any one of these three brain components requires a decrease in the volume of one or both of the remaining two components. Whenever the increase in volume is not offset by an equal decrease in volume, the brain is said to lose compliance, and the risk of elevated or abnormal intracranial pressure increases. Elevated intracranial pressure is associated with pathological sequela including cerebral ischemia and neurological deficits.

Attempts to estimate the mean cranial volume have produced results that vary based on differences in gender and methodology. For instance, using the Lee-Pearson formula, one investigation estimated mean cranial volume to be 1152.813±279.16 cubic centimeters ($cm^3$) in males and 1117.82±99.09 $cm^3$ in females. The same team reported similar results when estimating mean cranial volume using the spheroid formula: 1169.68±239.98 $cm^3$ for male subjects and 1081±111.6 $cm^3$ for female subjects. K. Y. Manjunath, Estimation of Cranial Volume in Dissecting Room Cadavers, *Journal of the Anatomical Society of India* Vol. 51, No. 2 (2002 July-2002 December). In contrast, using magnetic resonance (MR) image-based computerized segmentation, another investigation estimated mean intracranial volumes of 1469±102 $cm^3$ in men and 1289±111 $cm^3$ in women. Matsumae M, Kikinis R, Mórocz I A, Lorenzo A V, Sándor T, Albert M S, Black P M, Jolesz F A. Age-related changes in intracranial compartment volumes in normal adults assessed by magnetic resonance imaging. *J Neurosurg.* 1996 June; 84(6): 982-91.

The three components of the intracranial space—parenchyma, blood and CSF—respectively occupy approximately 80%, 10%, and 10% of the available volume. Using the estimates above, brain parenchyma occupies approximately 880-1120 cm$^3$ of volume; and blood and CSF each occupy approximately 110-140 cm$^3$.

Of the three volumetric components, blood volume can most readily be reduced through venous circulation. In contrast, parenchymal volume is regarded the least reducible as brain volume is not readily compressible. The reducibility of CSF volume occupies the intermediate tier between blood and parenchyma.

The choroid plexuses of the lateral and fourth ventricles continually produces CSF in the subarachnoid space at a rate of approximately 21-29 mL per hour (500-700 mL per day). CSF is absorbed into either the venous system or lymphatic system at a rate of approximately the same rate as production. The absorption of CSF therefore helps maintain a constant volume by offsetting the constant production of CSF.

The constancy of volume also maintains a constant ICP. However, the contribution of CSF reabsorption in lowering ICP is small because of the relatively slow rate of CSF reabsorption. Notably, CSF reabsorption can be slowed or interrupted in pathological conditions such as brain tumors, cysts, scarring, infection or the presence of blood in the subarachnoid space. Under normal conditions, CSF is renewed approximately four times each day.

C. ICP Waveforms

ICP manifests as a waveform consisting of three peaks in each wave. The first peak (referred to as either "P1," "$W_1$," or a "percussion wave") represents the arterial pulse transmitted through the choroid plexus into the CSF. The second peak (referred to as either "P2," "$W_2$," or a "tidal wave") represents intracranial compliance. The third peak (referred to as either "P3," "$W_3$," or a "dicrotic wave") correlates with the closure of the aortic valve.

Figure 2:
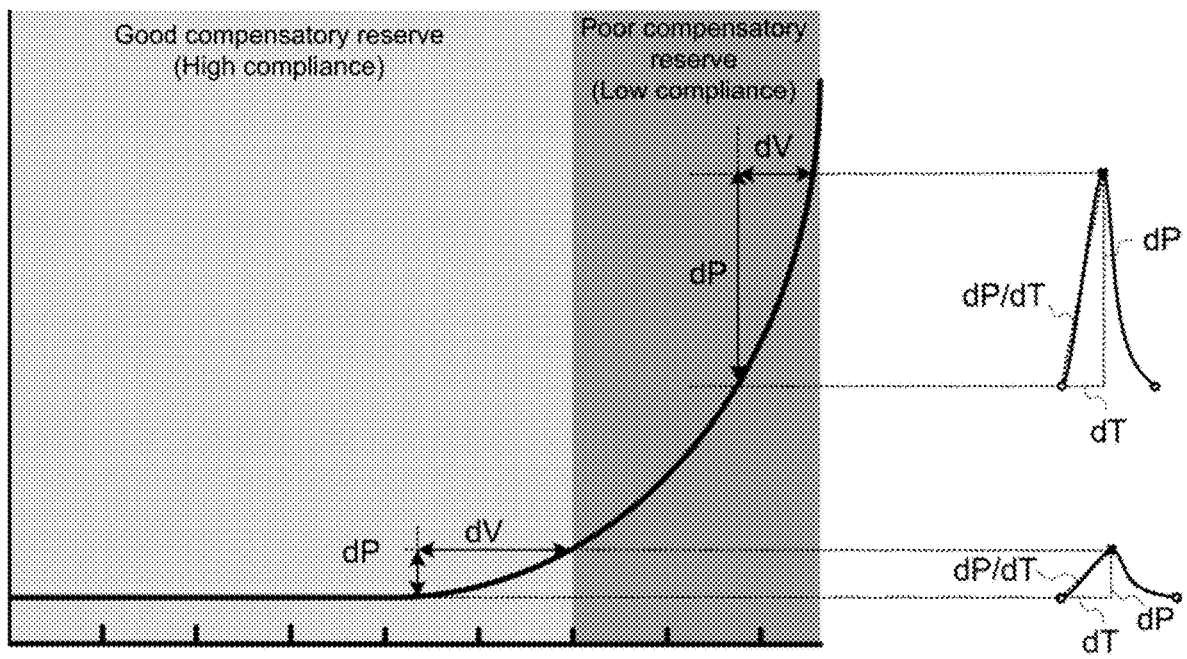
FIG. 2 is an illustration of the ICP-volume curve and its relationship to intracranial pulsatility parameters. (Eide 2010)

Small changes in intracranial volume associated with cardiac pulsations, believed to fall within in the range of 0.5-1 ml, generate small-amplitude peaks (dP) in the ICP waveform. As the total volume of components within the cranial vault increases, intracranial compliance begins to decrease. Mean ICP increases approximately exponentially with increases in intracranial volume. The diminishment of compliance is indicated by large-amplitude ICP waveform peaks (dP) in response to cardiac pulsations, shortening rise times (dT), and increasing ICP rise time coefficients (dP/dT). Eide P K, Rapoport B I, Gormley W B, Madsen J R. "A dynamic nonlinear relationship between the static and pulsatile components of intracranial pressure in patients with subarachnoid hemorrhage." *J Neurosurg*. 2010; 112(3):616-625. The ICP-volume curve and its relationship to the intracranial pulsatility parameters are depicted in FIG. 2.

D. Abnormal ICP (1) Lundberg Waves in Abnormal ICP

ICP can be characterized through Lundberg waves.

a. Lundberg A Waves

Lundberg A waves (also known as "plateau waves") are characterized by a steep rise in ICP from near normal values to 50 mmHg or more, and persisting for 5-20 minutes before falling sharply. Lundberg A waves are believed to arise from an increase in cerebrovascular volume due to vasodilation. Lundberg A waves occur and resolve in four phases. First, during the "drift phase," a decrease in cerebral perfusion pressure results in vasodilation. Second, during the "plateau phase," vasodilation results in increased ICP. Third, during the "ischemic response phase," the decrease in cerebral perfusion pressure produces cerebral ischemia of brainstem vasomotor centers, thereby eliciting Cushing's response. Fourth, Cushing's response restores cerebral perfusion pressure.

Cushing's response is a hypothalamic response to brain ischemia wherein the sympathetic nervous system is activated, which causes increased peripheral vascular resistance with a subsequent increase in systemic blood pressure. The increased blood pressure then activates the parasympathetic nervous system via carotid artery baroreceptors, resulting in vagal-induced bradycardia.

Cushing's response is believed to be a protective mechanism in which systemic blood pressure attempts to rise above ICP to maintain cerebral perfusion pressure (CPP), the net pressure gradient that drives oxygen delivery to cerebral tissue. CPP is the arithmetic difference between mean arterial pressure (MAP) and intracranial pressure (ICP), measured in millimeters of mercury (mmHg).

2. Lundberg B Waves

Lundberg B waves are characterized by rhythmic oscillations that last between 0.5 and 3 minutes in which the mean wave amplitude ICP ranges between 20-50 mmHg.

3. Lundberg C Waves

Lindberg C waves occur 4-8 times per minute and exhibit a lower amplitude than B waves.

(2) ICP Pulsatility

Mean (static) ICP is a poor indicator of intracranial pulsatility. In nearly 40% of the studied observations, a clinically low mean ICP was associated with a high mean wave amplitude and vice versa. Static and pulsatile ICP correlated well only over short intervals; the degree of correlation weakened over periods of hours and was inconsistent across patients and within individual patients over time.

In patients with SAH, the acute clinical state and final outcome were worse when pulsatile ICP was high even though the mean ICP was maintained within normal limits. Reducing pulsatile ICP improved the clinical state even though the mean ICP was within the normal range.

Patients with intracerebral hemorrhages with normal mean ICP (<15 mmHg) nonetheless have exhibited reduced intracranial compliance in the presence of high pulsatile ICP (>5 mmHg). In SAH patients, worsened clinical state was associated with high pulsatile ICP even though the mean ICP was normal. Administration of hypertonic saline to SAH patients for the reduction of ICP, produced no significant correlation between the change in static and pulsatile ICPs. (Eide 2010).

(3) Pressure-Time Dose

Figure 3:
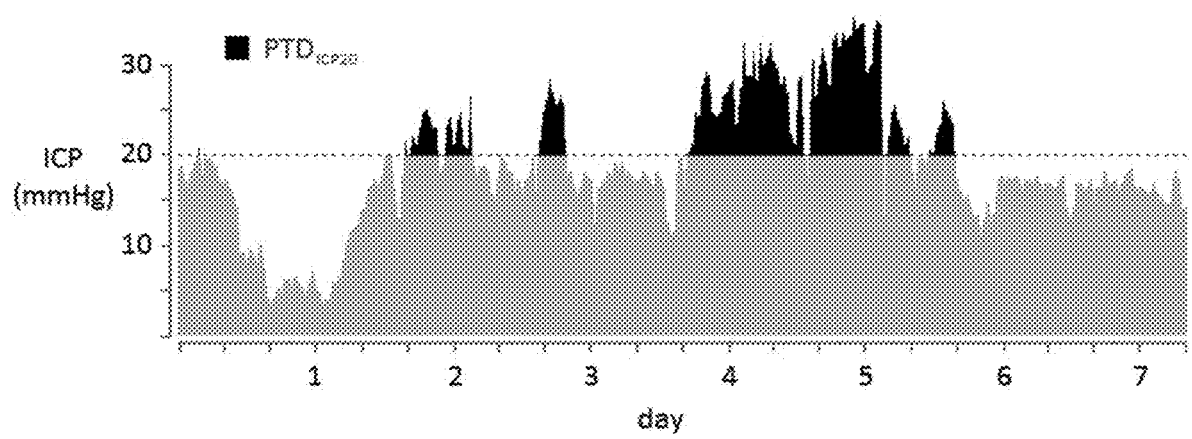
FIG. 3 is an illustration of the time course of intracranial pressure (ICP) in a patient. The dashed line indicates a threshold of 20 mmHg used to calculate $PTD_{ICP20}$. The black area represents $PTD_{ICP20}$. The grey area indicates the subthreshold ICP. PTD indicates pressure-time dose. (Magni 2015)

ICP can also be quantified through pressure-time dose (PTD). A PTD computes a cumulative dose of secondary injury by integrating the cumulative area under the curve (AUC) above or below a defined physiological threshold. The time course of intracranial pressure (ICP) in a patient is illustrated in FIG. 3. The dashed line indicates a threshold of 20 mmHg used to calculate $PTD_{ICP20}$. The black area represents $PTD_{ICP20}$. The grey area indicates the subthreshold ICP. PTD indicates pressure-time dose (Magni 2015).

The pressure-time dose of ICP ($PTD_{ICP}$) describes the extent of exposure to an ICP above a predetermined threshold, both in terms of length of time and intensity, describing both the cumulative amplitude and duration of episodes both above and below the selected threshold. PTD is measured in millimeters of mercury hours (mmHg·h). The selected threshold is annotated in subscript form beside the subscript "ICP"; for example, the $PTD_{ICP}$ for 30 mmHg is written as "$PTD_{ICP30}$."

A PTD$_{ICP}$ value for a subject is deemed "moderate" if the subject's PTD$_{ICP}$ value is greater than the median value of the PTD$_{ICP}$ distribution. Magni et al. observed a median PTD$_{ICP30}$ of 1 mmHg·h among 55 aSAH patients. Moderate PTD$_{ICP30}$ (HR 3.58, 95% CI 1.30-9.82, P=0.05) were significant prognostic factors of 6-month unfavorable outcome. Magni F, et al. High-Resolution Intracranial Pressure Burden and Outcome in Subarachnoid Hemorrhage. *Stroke.* 2015; 46(9):2464-2469.

E. Sequela of Abnormal ICP

Abnormal ICP is associated with the risk of diminished outcomes, such as death or neurological deficits. Mechanisms believed to give rise to such risks include brain shift and cerebral ischemia.

Sequelae known to follow abnormal ICP include ischemic deficits, poor neurological outcomes, and even death. Yet, despite the critical clinical significance of abnormal ICP, present treatment options remain limited.

F. Treatments for Abnormal ICP

There currently exists a large number of approved and experimental treatment options for disturbed cerebral homeostasis presenting as abnormal ICP. Such treatment options include but are not limited to: hyperosmolar agents (such as hypertonic saline or mannitol); CSF drainage; analgesics and sedatives (such as intravenous propofol; etomidate or midazolam for sedation; morphine or alfentanil for analgesia and antitussive effect); neuromuscular blockade; nimodipine and hyperventilation. Additionally, in patients with refractory intracranial hypertension, additional treatment options include: induction of barbiturate coma (with agents such as pentobarbital), steroids, optimized hyperventilation, hypothermia, resections of mass lesions, and decompressive craniectomy. However, these treatments suffer from serious drawbacks and potentially life-threatening side effects.

4. Hydrocephalus

Hydrocephalus refers to an abnormal accumulation of cerebrospinal fluid (CSF) within the ventricles of the brain. Hydrocephalus can lead to abnormal ICP, which damages the brain and can lead to death, however, hydrocephalus also occurs in the absence of elevated ICP.

A large number of surgical and medical interventions are available to treat hydrocephalus. A nonlimiting list of examples of surgical interventions include placement of a shunt, endoscopic third ventriculostomy (ETV), ablation of the choroid plexus. Nonlimiting illustrative examples of nonsurgical treatments include osmotic agents (e.g. theobromine, isorbide, glycerol, mannitol, erythritol); acetazolamide (monotherapy or with furosemide); ion channel blockers (e.g., digoxin, triamterene, TRPV4 antagonists); steroids (glucocorticoids, betamethasone, dexamethasone, methylprednisolone); radioactive agents (to destroy the choroid plexus); thrombolytic agents (e.g., urokinase or streptokinase); anti-inflammatory agents (e.g., prednisolone, methylprednisolone, corticosteroid therapy, anakinra, minocycline, ibuprofen, pioglitazone, or infliximab); transforming growth factor β antagonists (e.g., recombinant human hepatocyte growth factor); deferoxamine; matrix metalloproteinases (e.g., hyaluronidase); vasoactive drugs (nimodipine, magnesium, isosorbide dinitrate); VEGF antagonists (e.g., bevacizumab); and antioxidative agents (e.g., epigallocatechin gallate, N-acetylcystein, melatonin, alpha-tocopherol, L-ascorbic acid, coenzyme Q10, reduced glutathione, reduced lipoic acid, catechin polyphenols from *Camellia sinensis*, edaravone).

The nonsurgical treatments are largely experimental and have not been validated by clinical trials. There thus remains a long unmet need for noninvasive treatments for hydrocephalus.

5. Isoquinoline Derivatives

A. Characterization

For over three decades, isoquinoline derivatives have been studied extensively as potential therapeutic agents. Cedric Logé, Xavier Siomboing, Valérie Wallez, Elizabeth Scalbert, Caroline Bennejean, Christelle Cario-Tourmaniantz, Gervaise Loirand, Bernard Gressier, Pierre Pacaud & Michel Luyckx (2003) Synthesis and Pharmacological Study of Rho-Kinase Inhibitors: Pharmacomodulations on the Lead Compound Fasudil, *Journal of Enzyme Inhibition and Medicinal Chemistry,* 18:2, 127-138, DOI: 10.1080/14756360310000935561.

Isoquinoline derivatives have been known to inhibit the activity of kinases including CaMKII, cyclic AMP-dependent protein kinase, MSK1, PRK-2, protein kinase C, and rho-associated coiled-coil containing kinases (e.g., ROCK-1 and ROCK-2).

In animal and human studies, isoquinoline derivatives have been seen to exert a vasodilatory effect.

Nonlimiting examples of isoquinoline derivatives are disclosed in the following references, which are each herein incorporated by reference in their respective entireties: "Substituted isoquinolines and isoquinolinones as Rho kinase inhibitors" (U.S. Pat. No. 8,541,449); "Substituted isoquinoline and isoquinolinone derivatives" (U.S. Pat. No. 8,461,144); "6-substituted isoquinolines and isoquinolinones" (U.S. Pat. No. 8,399,482); "Piperidinyl-Substituted Isoquinolone Derivatives" (U.S. Pat. No. 8,188,117); "Isoquinoline derivatives" (U.S. Pat. No. 7,618,985); "Isoquinoline derivatives and drugs" (U.S. Pat. No. 6,153,608); "1-(5-isoquinolinesulfonyl)homopiperazine hydrochloride hydrates" (U.S. Pat. No. 5,942,505); "Derivatives of isoquinoline (and naphthalene) sulfonamides" (U.S. Pat. No. 5,216,150); "Isoquinoline derivatives" (U.S. Pat. No. 4,798,897); "Substituted isoquinolinesulfonyl compounds" (U.S. Pat. No. 4,678,783); "Isoquinolinesulfonyl derivatives" (U.S. Pat. No. 4,525,589); "Prodrugs of 1-(1-hydroxy-5-isoquinolinesulfonyl) homopiperazine" (U.S. patent application Ser. No. 10/857,572); "Substituted isoquinolinesulfonyl compounds" (European Patent No. EP0187371); "Isoquinoline derivatives" (European Patent No. EP0287696); "Isoquinolinesulfonamide derivatives and drugs containing the same as the active ingredient" (Canadian Patent Application No. CA2327276); and "Quinolinesulphonamides having smooth muscle relaxation activity" (U.K. Patent Application No. 9122595.3).

B. Methods for Treatment

Disclosed herein are methods for the use of an isoquinoline derivative to treat disturbances to cerebral homeostasis. The present disclosure further provides methods for treating or preventing disturbed cerebral homeostasis using isoquinoline sulfonamide derivatives that can regulate vascular activity by modulating the activity of one or more rho-associated coiled-coil containing kinases. Such derivatives are known in the art and can be synthesized by known methods or commercially obtained from available vendors. The first such derivative to be approved for clinical use was fasudil (FIG. 1). Subsequent derivatives include ripasudil; netarsudil; BA-1041, BA-1042, BA-1043, and BA-1049 (U.S. Pat. No. 10,106,525); FSD-C10 (Xin 2013); H7, H8, and H89 (Lochner & Moolman 2006); and H1152P (Breitenlechner 2003). Alternatively, disclosed herein are methods for the improvement of patient outcome in subjects who have experienced disturbed cerebral homeostasis, are presently experiencing disturbed cerebral homeostasis, or are at risk of disturbed cerebral homeostasis.

Disclosed herein are methods for use of an isoquinoline derivative in the manufacture of a medicament for the treatment of disturbances to cerebral homeostasis.

Disclosed herein are isoquinoline derivatives for use in treating disturbances to cerebral homeostasis.

Disclosed herein are isoquinoline derivatives for use as a medicament for treating disturbances to cerebral homeostasis.

According to some embodiments, the subject has, or is at risk of, or presents sign(s) and/or symptom(s) of any one or any combination of the following: abnormal activity in α-blocker substrates; abscess; benign intracranial hypertension; a brain injury (either traumatic, non-traumatic or both) that deposits blood in the subarachnoid space; brain tumor; choroid plexus tumor; contusions; depression fractures over major venous sinuses causing obstruction; diffuse traumatic brain/head injury; disturbances with CSF dynamics; early brain injury before onset of vasospasm; encephalitis; epileptic seizures; expansion of hematomas; focal edema secondary to trauma; global cerebral edema; heart failure; hydrocephalus (including communicating hydrocephalus, obstructive hydrocephalus, normal-pressure hydrocephalus, and hydrocephalus ex-vacuo); infarction; intracerebral hemorrhage; intracranial hemorrhage; intraventricular hemorrhage; intraparenchymal hemorrhage; lead encephalopathy; metabolic/hypertensive encephalopathy; meningeal infiltration; meningitis; near drowning; neuroinflammation; paralytic ileus; Reye's syndrome; ruptured aneurysm; spinal cord injury; subarachnoid hemorrhage (including aneurysmal subarachnoid hemorrhage or other non-traumatic subarachnoid hemorrhages); subdural hematoma; symptomatic vasospasm; traumatic brain injury, traumatic hematomas (extradural, subdural, intracerebral), tumors or neoplasms (e.g., glioma, meningioma, metastasis); unruptured aneurysm; vasculitis; venous sinus thrombosis/cerebral venous thrombosis; or water intoxication.

According to some embodiments, the subject has, or is at risk of having, low systolic blood pressure. According to some embodiments, the subject, if administered a drug that is not an isoquinoline derivative, will have, or will be at risk of having, low systolic blood pressure. According to some embodiments, said low systolic blood pressure is blood pressure of less than 90 mmHg, less than 89 mmHg, less than 88 mmHg, less than 87 mmHg, less than 86 mmHg, less than 85 mmHg, less than 84 mmHg, less than 83 mmHg, less than 82 mmHg, less than 81 mmHg, less than 80 mmHg, less than 79 mmHg, less than 78 mmHg, or less than 77 mmHg.

According to some embodiments, the subject has, or is at risk of having, a low cerebral perfusion pressure. According to some embodiments, the subject, if administered a drug that is not an isoquinoline derivative, will have, or will be at risk of having, a low cerebral perfusion pressure. According to some embodiments, said low cerebral perfusion pressure is cerebral perfusion pressure of less than 80 mmHg, less than 79 mmHg, less than 78 mmHg, less than 77 mmHg, less than 76 mmHg, less than 75 mmHg, less than 74 mmHg, less than 73 mmHg, less than 72 mmHg, less than 71 mmHg, less than 70 mmHg, less than 69 mmHg, less than 68 mmHg, less than 67 mmHg, less than 66 mmHg, less than 65 mmHg, less than 64 mmHg, less than 63 mmHg, less than 62 mmHg, less than 61 mmHg, less than 60 mmHg, less than 59 mmHg, less than 58 mmHg, less than 57 mmHg, less than 56 mmHg, less than 55 mmHg, less than 54 mmHg, less than 53 mmHg, less than 52 mmHg, less than 51 mmHg, less than 50 mmHg, less than 49 mmHg, less than 48 mmHg, less than 47 mmHg, less than 46 mmHg, or less than 45 mmHg.

According to some embodiments, the subject has, or is at risk of having, a low brain tissue oxygen pressure ($P_{bt}O_2$). According to some embodiments, the subject, if administered a drug that is not an isoquinoline derivative, will have, or will be at risk of having, a low brain tissue oxygen pressure. According to some embodiments, said low brain tissue oxygen pressure is a $P_{bt}O_2$ of less than 20 mmHg, less than 19 mmHg, less than 18 mmHg, less than 17 mmHg, less than 16 mmHg, less than 15 mmHg, less than 14 mmHg, less than 13 mmHg, less than 12 mmHg, less than 11 mmHg, or less than 10 mmHg.

According to some embodiments, the subject has, or is at risk of having, pathological values for parameters derived from cerebral microdialysis (CMD). According to some embodiments, the subject, if administered a drug that is not an isoquinoline derivative, will have, or will be at risk of having, pathological values for parameters derived from cerebral microdialysis. According to some embodiments, said pathological values include any one or more of the following: CMD-glucose<0.7 mmol/l; CMD-lactate>4 mmol/l; CMD-pyruvate<120 µmol/l; CMD-glutamate>10 µmol/l; CMD-glycerol>50 µmol/l, and CMD-lactate-to-pyruvate-ratio>40.

According to some embodiments, any one or any combination of the following treatments are not adjudged medically appropriate for the subject: 17β-estradiol (E2), abobotulinumtoxinA, aspirin, botulinum toxin, calcium-channel blocker, cilostazol, clazosentan, dantrolene, enalapril, endothelin-1 antagonist, endothelin receptor antagonist, erythropoietin, estrogen, $ET_A$ receptor antagonist, ETB receptor antagonist, enoxaparin, heparin, hormone, hydralazine, L-type calcium-channel blocker, labetalol, magnesium, milrinone, nicardipine, nimodipine, nitric oxide, nitric oxide progenitors, papaverine, phosphodiesterase inhibitors, pravastatin, recombinant tissue plasminogen activator, sildenafil, simvastatin, statin, TAK-044, tirilazad, tissue plasminogen activator, or verapamil. According to some embodiments, the subject is under an NPO, NBM, or complete-bowel-rest order.

According to some embodiments, the subject has, or is at risk of having, detectable focal enhancement in the leptomeningeal compartment using 3-tesla T2-weighted, fluid-attenuated inversion recovery (FLAIR) MRI. According to some embodiments, the subject has, or is at risk of having, detectable T2 signal hyperintensity in the leptomeningeal compartment, the parenchyma or the intracranial vasculature. According to some embodiments, the MM is noncontrast or postcontrast.

According to some embodiments, the subject has, or is at risk of having, an erythrocyte sedimentation rate (ESR) of: over 15 mm/hr; over 16 mm/hr; over 17 mm/hr; over 18 mm/hr; over 19 mm/hr; over 20 mm/hr; over 21 mm/hr; over 22 mm/hr; over 23 mm/hr; over 24 mm/hr; over 25 mm/hr; over 26 mm/hr; over 27 mm/hr; over 28 mm/hr; over 29 mm/hr; or over 30 mm/hr.

According to some embodiments, the subject has, or is at risk of having, a serum C-reactive protein concentration of over: 0.8 mg/L; 0.9 mg/L; 1.0 mg/L; 1.1 mg/L; 1.2 mg/L; 1.3 mg/L; 1.4 mg/L; 1.5 mg/L; 1.6 mg/L; 1.7 mg/L; 1.8 mg/L; 1.9 mg/L; 2.0 mg/L; 2.1 mg/L; 2.2 mg/L; 2.3 mg/L; 2.4 mg/L; 2.5 mg/L; 2.6 mg/L; 2.7 mg/L; 2.8 mg/L; 2.9 mg/L; 3.0 mg/L; or 3.1 mg/L.

According to some embodiments, the subject is an adult who, in the lateral decubitus position with the legs and neck in a neutral position, will have an opening pressure of above 200 mm $H_2O$ or 250 mm $H_2O$ in response to a lumbar puncture.

According to some embodiments, the subject has, or is at risk of having, cerebrospinal fluid protein of 19 to 2110 mg/dL. According to some embodiments, the subject has, or is at risk of having, cerebrospinal fluid protein of 50-400 mg % in response to an early lumbar tap relative to ictus. According to some embodiments, the subject has cerebrospinal fluid protein of 100-800 mg % in response to an late lumbar tap relative to ictus.

According to some embodiments, the subject has, or is at risk of having, within 72 hours of presentation, a leukocyte count of greater than: $9.5 \times 10^9$/L, $10.0 \times 10^9$/L, $12.1 \times 10^9$/L, $13.3 \times 10^9$/L, or $13.84 \times 10^9$/L.

According to some embodiments, the subject has, or is at risk of having, a percentage of polymorphonuclear cells of greater than 65.2% or greater than 76.7%.

According to some embodiments, the subject has a history of: severe cerebrovascular disease; moyamoya disease; giant aneurysm; recent previous subarachnoid hemorrhage; and/or severe cardiopulmonary, hepatorenal, or metabolic diseases (such as diabetes mellitus). According to some embodiments, the subject did not undergo a procedure for securing a ruptured aneurysm within 1 day after SAH, 2 days after SAH, 3 days after SAH, 4 days after SAH, 5 days after SAH, 6 days after SAH, 7 days after SAH, 8 days after SAH, 9 days after SAH, 10 days after SAH, or later.

According to some embodiments, the subject presents with no evidence of infection, cancer, metabolic disease, space-occupying mass, giant aneurysm, neurodegenerative disease, or subclinical hematologic disease.

According to some embodiments, the subject is classified with a Hunt-Hess Grade or Hunt & Kosnik Grade of 1, 2, 3, 4, 5, 1-2, 1-3, 1-4, 1-5, 2-3, 2-4, 2-5, 3-4, 3-5, 4-5, or any combination thereof.

According to some embodiments, the subject does not have, and/or is not at risk of developing any one or more of the following: acute phase vasospasm, angiographic vasospasm, cerebral infarction, cerebral vasospasm, cerebrovascular spasms, delayed cerebral ischemia (DCI), delayed ischemic neurological deficit, non-acute vasospasm, non-clinical vasospasm, or ischemia from large capacitance cerebral arteries.

According to some embodiments, the diameter of any of the subject's large capacitance cerebral vessels does not narrow to, or is not at risk of narrowing to, 95% or more, 90% or more, 85% or more, 80% or more, 75% or more, 70% or more, 65% or more, 60% or more, 55% or more, 50% or more, 45% or more, 40% or more, 35% or more, 30% or more, 25% or more, 20% or more, 15% or more, 10% or more, 5% or more, or more than 0%, of the diameter observed on admission of the respective cerebral vessel.

According to some embodiments, the diameter of any of the subject's large capacitance cerebral vessels does not narrow to, or is not at risk of narrowing to less than 100%, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, or 5% or less, of the diameter observed on admission of the respective cerebral vessel.

According to some embodiments, the subject does not have, and/or is not at risk of developing, cerebral vasospasm by day 1 post-ictus, day 2 post-ictus, day 3 post-ictus, day 4 post-ictus, day 5 post-ictus, day 6 post-ictus, day 7 post-ictus, day 8 post-ictus, day 9 post-ictus, day 10 post-ictus, day 11 post-ictus, day 12 post-ictus, day 13 post-ictus, day 14 post-ictus, day 15 post-ictus, day 16 post-ictus, day 17 post-ictus, day 18 post-ictus, day 19 post-ictus, day 20 post-ictus, day 21 post-ictus, day 22 post-ictus, day 23 post-ictus, day 24 post-ictus, day 25 post-ictus, day 26 post-ictus, day 27 post-ictus, day 28 post-ictus, day 29 post-ictus, day 30 post-ictus, or later.

According to some embodiments, the subject has, or is at risk of having: an aneurysm located in anterior circulation, posterior circulation, the anterior communicating artery, the posterior communicating artery, the middle cerebral artery, the basilar artery, or the vertebral artery.

According to some embodiments, the subject has, or is at risk of having, an aneurysm located anterior to the central sulcus.

According to some embodiments, the subject has, or is at risk of having, a mean ICP of over 5 mmHg, over 6 mmHg, over 7 mmHg, over 8 mmHg, over 9 mmHg, over 10 mmHg, over 11 mmHg, over 12 mmHg, over 13 mmHg, over 14 mmHg, 15 mmHg, over 16 mmHg, over 17 mmHg, over 18 mmHg, over 19 mmHg, over 20 mmHg, over 21 mmHg, over 22 mmHg, over 23 mmHg, over 24 mmHg, over 25 mmHg, over 26 mmHg, over 27 mmHg, over 28 mmHg, over 29 mmHg, over 30 mmHg, over 31 mmHg, over 32 mmHg, over 33 mmHg, over 34 mmHg, over 35 mmHg, over 36 mmHg, over 37 mmHg, over 38 mmHg, over 39 mmHg, over 40 mmHg, or higher.

According to some embodiments, the subject has, or is at risk of having: large-amplitude ICP waveform peaks (dP); shortened ICP waveform rise times (dT); increased ICP rise time coefficients (dP/dT); pulsatile ICP of greater than 5 mmHg.

According to some embodiments, the subject has, or is at risk of having, pulsatile ICP waveforms of over 2 mmHg, over 3 mmHg, over 4 mmHg, over 5 mmHg, over 6 mmHg, over 7 mmHg, over 8 mmHg, over 9 mmHg, over 10 mmHg, or higher.

According to some embodiments, the subject has, or is at risk of having, a pulsatile ICP greater than: 5 mmHg, 6 mmHg, 7 mmHg, 8 mmHg, 9 mmHg, 10 mmHg, 11 mmHg, 12 mmHg, 13 mmHg, 14 mmHg, 15 mmHg, or more.

According to some embodiments, the subject has, or is at risk of having: abnormal ICP; angiogram-negative SAH; perimesencephalic SAH; or no arteriographic vasospasm.

According to some embodiments, the abnormal ICP is the result of physical trauma, is due to a ruptured aneurysm, is due to an unruptured aneurysm, is due to arteriovenous malformation, or occurs spontaneously. According to some embodiments, the aneurysm is graded as small (less than 15 mm), large (15-25 mm) or giant (greater than 25 mm).

According to some embodiments, the abnormal ICP consists of any of P1, P2, or P3 being greater than: 1 mmHg, 2 mmHg, 3 mmHg, 4 mmHg, 5 mmHg, 6 mmHg, 7 mmHg, 8 mmHg, 9 mmHg, 10 mmHg, or more. According to some embodiments, the subject has, or is at risk of having: rounded waveforms or a P2 amplitude higher than P1.

According to some embodiments, any of P1, P2, or P3 are greater than: 10% of the mean ICP, 11% of the mean ICP, 12% of the mean ICP, 13% of the mean ICP, 14% of the mean ICP, 15% of the mean ICP, 16% of the mean ICP, 17% of the mean ICP, 18% of the mean ICP, 19% of the mean ICP, 20% of the mean ICP, 21% of the mean ICP, 22% of the mean ICP, 23% of the mean ICP, 24% of the mean ICP, 25% of the mean ICP, 26% of the mean ICP, 27% of the mean ICP, 28% of the mean ICP, 29% of the mean ICP, 30% of the mean ICP, 31% of the mean ICP, 32% of the mean ICP, 33% of the mean ICP, 34% of the mean ICP, 35% of the mean ICP, 36% of the mean ICP, 37% of the mean ICP, 38% of the mean ICP, 39% of the mean ICP, or 40% of the mean ICP.

According to some embodiments, the subject has, or is at risk of having, a $PTD_{ICP30}$ of over 0.9 mmHg·hrs, over 1.0 mmHg·hrs, over 1.1 mmHg·hrs, over 1.2 mmHg·hrs, over 1.3 mmHg·hrs, over 1.4 mmHg·hrs, over 1.5 mmHg·hrs, over 1.6 mmHg·hrs, over 1.7 mmHg·hrs, over 1.8 mmHg·hrs, over 1.9 mmHg·hrs, over 2 mmHg·hrs, over 3 mmHg·hrs, over 4 mmHg·hrs, over 5 mmHg·hrs, over 6 mmHg·hrs, over 7 mmHg·hrs, over 8 mmHg·hrs, over 9 mmHg·hrs, over 10 mmHg·hrs, over 11 mmHg·hrs, over 12 mmHg·hrs, over 13 mmHg·hrs, over 14 mmHg·hrs, over 15 mmHg·hrs, or higher.

According to some embodiments, the subject has, or is at risk of having: Lundberg A waves. According to some embodiments, said Lundberg A waves are accompanied by a steep rise in ICP from near normal levels to between 20 mmHg and 50 mmHg. According to some embodiments, said Lundberg A waves persist between 5 minutes to 30 minutes before falling rapidly.

According to some embodiments, the subject has, or is at risk of having: Lundberg B waves. According to some embodiments, said Lundberg B waves are accompanied by a rise in ICP from near normal levels to between 20 mmHg and 50 mmHg. According to some embodiments, said Lundberg B waves persist between 0.5 minutes to 3 minutes before returning to normal.

According to some embodiments, the subject either is unable to tolerate or has been determined to be unable to tolerate nimodipine. According to some embodiments, the subject was discontinued from nimodipine treatment or had previously received nimodipine. According to some embodiments, the subject is suffering from or is at risk of systemic hypotension. According to some embodiments, the subject has developed or is expected to develop dose-limiting hypotension in response to nimodipine. According to some embodiments, said nimodipine is administered intravenously or parenterally or enterically. According to some embodiments, said nimodipine is administered in a 30 mg dose or a 60 mg intravenous dose. According to some embodiments, said nimodipine is administered once every four hours.

Published literature reports that "neurologists in Asia consider that lower doses of IV tPA are better for Asian patients with stroke because of the racial difference in coagulation and fibrinolysis responses . . . . Consequently, Japan is the only nation that recommends 0.6 mg/kg of IV tPA in its stroke care guideline." (Dong 2016.) According to some embodiments, the subject is not expected to or does not exhibit coagulation and fibrinolysis responses typical of Asian populations.

According to some embodiments, the subject is treated under the standards-of-care of either North America or Europe. According to some embodiments, the subject is not treated under the standards-of-care of Japan or China. According to some embodiments, the subject is treated in either North America or Europe. According to some embodiments, the subject is not treated in Japan or China.

According to some embodiments, the isoquinoline derivative is GSK269962A, SB772077B, SLx-2119, SR-715, SR-899, Y-27632, Y 32885, Y-39983, belumosudil, dimethylfasudil, fasudil, hydroxyfasudil, netarsudil, or ripasudil. According to some embodiments, hydroxyfasudil is administered using fasudil as a prodrug.

According to some embodiments, the isoquinoline derivative as described herein is administered as a pure chemical. According to some embodiments, the isoquinoline derivative described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science & Practice of Pharmacy* (22nd ed. 2012).

According to some embodiments, provided herein is a pharmaceutical composition comprising at least one isoquinoline derivative, or a stereoisomer, pharmaceutically acceptable salt, hydrate, anhydrate, hemi-hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the patient.

According to some embodiments, the isoquinoline derivative is substantially pure, in that it contains less than about 5%, or less than about 1%, or less than about 0.1%, of other organic small molecules, such as unreacted intermediates or synthesis by-products that are created, for example, in one or more of the steps of a synthesis method.

According to some embodiments, suitable oral dosage forms include, for example, tablets, pills, sachets, or capsules of hard or soft gelatin, methylcellulose or of another suitable material easily dissolved in the digestive tract. According to some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. See, e.g., *Remington* (22nd ed. 2012).

According to some embodiments, the disclosure provides a pharmaceutical composition for injection containing a isoquinoline derivative or a salt thereof and a pharmaceutical excipient suitable for injection. Components and amounts of agents in the composition are as described herein.

According to some embodiments, the forms in which the novel composition of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution (including sterile saline solutions), and similar pharmaceutical vehicles.

According to some embodiments, aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

According to some embodiments, sterile injectable solutions are prepared by incorporating the compound of the present disclosure in the required amount in the appropriate solvent with various other ingredients as enumerated above, as required, followed by filtered sterilization, moist terminal sterilization or dry terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

According to some embodiments, compositions for inhalation or insufflation include solutions and suspensions in pharmaceutically acceptable, aqueous or organic solvents, or mixtures thereof, and powders. The liquid or solid composition may contain suitable pharmaceutically acceptable excipients as described supra. A composition in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

According to some embodiments, a pharmaceutical composition may also be prepared from composition described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Knoben & Troutman, eds., *Handbook of Clinical Drug Data*, McGraw-Hill (10th ed. 2002); Pratt and Taylor, eds., *Principles of Drug Action* (3d ed. 1990); Katzung, ed., *Basic and Clinical Pharmacology* (9th ed. 2003); Goodman and Gilman, eds., *The Pharmacological Basis of Therapeutics* (10th ed. 2001); Remington (22nd ed. 2012); Martindale, The Extra Pharmacopoeia, Thirty-Second Edition (The Pharmaceutical Press, London, 1999); all of which are incorporated by reference herein in their entirety.

According to some embodiments, dosage forms of the present disclosure may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Diluents can be incorporated into the tablet core of a dosage form. Dosage forms of the invention, preferably a tablet core matrix, optionally comprise one or more pharmaceutically acceptable diluents as excipients. Non-limiting examples of suitable diluents include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of amorphous cellulose (e.g., Rexcel™) and powdered cellulose; calcium carbonate; glycine; bentonite; polyvinylpyrrolidone; and the like. Such diluents, if present, constitute in total about 5% to about 99%.

According to some embodiments, pharmaceutically acceptable carriers for therapeutic use are well known in the pharmaceutical art, and are described, for example, in *Remington* (22nd ed. 2012). Preservatives, stabilizers, dyes and other ancillary agents may be provided in the pharmaceutical composition. For example, sodium benzoate, sorbic acid and esters of p-hydroxybenzoic acid may be added as preservatives. In addition, antioxidants and suspending agents may be used.

According to some embodiments, in addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, and magnesium aluminum silicate.

According to some embodiments, the pharmaceutical composition is formulated in a dosage form for administration. Examples of pharmaceutically acceptable compositions include compositions that do not require reconstitution; a solution that does not contain glucose; a buffered solution; or a solution with a pH between 5-6, 6-7, 7-8, 8-9, or any combination of the foregoing pH ranges.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

Further, pharmaceutically acceptable salts of the compounds are contemplated and also may be utilized in the disclosed methods. For example, a carboxylic acid group of the disclosed compounds may be deprotonated and an amino group of the disclosed compounds may be protonated. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

"Pharmaceutically acceptable salt" includes both acid and base addition salts. A pharmaceutically acceptable salt of any one of the isoquinoline derivative described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogen-phosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitro-benzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, e.g., Berge S. M. et al., "Pharmaceutical Salts," *J. Pharma Sci.* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. (Berge 1997).

It should be recognized that the particular counter-ion forming a part of any salt of a compound disclosed herein is usually not of a critical nature, so long as the salt as a whole is pharmacologically acceptable and as long as the counter-ion does not contribute undesired qualities to the salt as a whole. Undesired qualities may include undesirable solubility or toxicity.

It will be further appreciated that the disclosed compounds can be in equilibrium with various inner salts. For example, inner salts include salts wherein the compound includes a deprotonated carboxyl group and a protonated amino group.

According to some embodiments, oral doses range from about 1.0 mg to about 1000 mg, one to four times, or more, per day.

According to some embodiments, the dose of the isoquinoline derivative or salt thereof may be about 1 mg to about 240 mg. The dose may be at least 1 mg, 2 mg, 3 mg, 4 mg, 5 mg, 10 mg, 15 mg, 20 mg, 30 mg, 40 mg, 45 mg, 50 mg, 60 mg, 120 mg, 150 mg, 180 mg, 240 mg, or more. The dose may be about 1 mg, 2 mg, 3 mg, 4 mg, 5 mg, 10 mg, 15 mg, 20 mg, 30 mg, 40 mg, 45 mg, 50 mg, 60 mg, 120 mg, 150 mg, 180 mg, 240 mg, or more. The dose may be at least or about 1 mg, 2 mg, 3 mg, 4 mg, 5 mg, 10 mg, 15 mg, 20 mg, 30 mg, 40 mg, 45 mg, 50 mg, 60 mg, 120 mg, 150 mg, 180 mg, 240 mg, or more. The dose may be in a range of about 1 mg to about 240 mg. The dose may be in a range of about 0.1 mg to about 1 mg, about 0.1 mg to about 5 mg, about 0.1 mg to about 10 mg, about 0.1 mg to about 15 mg, about 0.1 mg to about 20 mg, about 0.1 mg to about 30 mg, about 0.1 mg to about 40 mg, about 0.1 mg to about 45 mg, about 0.1 mg to about 60 mg, about 0.1 mg to about 120 mg, about 0.1 mg to about 180 mg, or about 0.1 mg to about 240 mg.

According to some embodiments, the dose of the composition comprising at least one isoquinoline derivative as described herein differ, depending upon the patient's (e.g., human) condition, that is, stage of the disease, general health status, age, and other factors.

According to some embodiments, the duration of treatment may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days or more. According to some embodiments, the specified duration may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 consecutive days or more. Administration may be 1, 2, 3, 4, or more times a day. Administration may be every 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. For example, for a 30 mg dose of isoquinoline derivative or salt thereof for a period of two weeks and administration 3 times a day, the total dosage of the isoquinoline derivative or salt thereof would be 1260 mg.

According to some embodiments, the treatment may entail a starting dose of isoquinoline derivative or a salt thereof over a period of time, wherein the starting dose can be escalated upward to a first escalated dose, a second escalated dose, a third escalated dose or a fourth escalated dose. According to some embodiments, the first escalated dose, second escalated dose, third escalated dose or fourth escalated dose may be 1.5 times, 1.75 times, 2 times, 2.5 times, 3.0 times, 3.5 times, 4.0 times, 4.5 times, 5.0 times, 5.5 times, 6.0 times, 6.5 times, 7.0 times, 7.5 times, 8.0 times, 8.5 times, 9.0 times, 9.5 times, 10 times, 11 times, or 12 times the starting dose. A number of different or non-identical escalated doses may be 1, 2, 3, 4, 5, 6, 7, 8, 9, 10, 11, or 12 escalated doses from a starting dose. An escalated dose may be 1.5 times, 2 times, 2.5 times, 3.0 times, 3.5 times, 4.0 times, 4.5 times, 5.0 times, 5.5 times, 6.0 times, 6.5 times, 7.0 times, 7.5 times, 8.0 times, 9.0 times, 9.5 times, 10 times, 11 times, or 12 times the starting dose. For example, if the starting dose is 1 mg, an escalated starting dose that is 6 times as high, is 6.0 mg.

According to some embodiments, the isoquinoline derivative is administered at or about a dose of: 1 mg, 5 mg, 10 mg, 15 mg, 20 mg, 30 mg, 40 mg, 45 mg, 50 mg, 60 mg, 70 mg, 75 mg, 80 mg, 90 mg, 100 mg, 105 mg, 110 mg, 120 mg, 130 mg, 135 mg, 140 mg, 150 mg, 160 mg, 165 mg, 170 mg, 180 mg, 190 mg, 195 mg, 200 mg, 210 mg, 220 mg, 225 mg, 230 mg, or 240 mg.

According to some embodiments, the isoquinoline derivative is administered at or about a dose of: 0.1 mg/kg; 0.2 mg/kg; 0.3 mg/kg; 0.4 mg/kg; 0.5 mg/kg; 0.6 mg/kg; 0.7 mg/kg; 0.8 mg/kg; 0.9 mg/kg; 1.0 mg/kg; 1.1 mg/kg; 1.2 mg/kg; 1.3 mg/kg; 1.4 mg/kg; 1.5 mg/kg; 1.6 mg/kg; 1.7 mg/kg; 1.8 mg/kg; 1.9 mg/kg; 2.0 mg/kg; or more.

According to some embodiments, the therapeutic amount of the isoquinoline derivative is at least about 1 mg, at least about 5 mg, at least about 10 mg, at least about 15 mg, at least about 20 mg, at least about 30 mg, at least about 40 mg, at least about 45 mg, at least about 50 mg, at least about 60 mg, at least about 70 mg, at least about 75 mg, at least about 80 mg, at least about 90 mg, at least about 100 mg, at least about 105 mg, at least about 110 mg, at least about 120 mg, at least about 130 mg, at least about 135 mg, at least about 140 mg, at least about 150 mg, at least about 160 mg, at least about 165 mg, at least about 170 mg, at least about 180 mg, at least about 190 mg, at least about 195 mg, at least about 200 mg, at least about 210 mg, at least about 220 mg, at least about 225 mg, at least about 230 mg, or at least about 240 mg or more.

According to some embodiments, the administered dose contains at least about 1 mg, at least about 5 mg, at least about 10 mg, at least about 15 mg, at least about 20 mg, at least about 30 mg, at least about 40 mg, at least about 45 mg, at least about 50 mg, at least about 60 mg, at least about 70 mg, at least about 75 mg, at least about 80 mg, at least about 90 mg, at least about 100 mg, at least about 105 mg, at least about 110 mg, at least about 120 mg, at least about 130 mg, at least about 135 mg, at least about 140 mg, at least about 150 mg, at least about 160 mg, at least about 165 mg, at least about 170 mg, at least about 180 mg, at least about 190 mg, at least about 195 mg, at least about 200 mg, at least about 210 mg, at least about 220 mg, at least about 225 mg, at least about 230 mg, or at least about 240 mg or more, of isoquinoline derivative.

According to some embodiments, the composition is administered in at least 2-3 administered doses, each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the isoquinoline derivative is administered once daily, twice daily, three times daily, four times daily, five times daily, six times daily, or eight times daily. According to some embodiments, the isoquinoline derivative is administered continuously without substantial interruption over the course of a day.

According to some embodiments, the isoquinoline derivative is administered at least 1 hour apart, at least 2 hours apart, at least 3 hours apart, at least 4 hours apart, at least 5 hours apart, at least 6 hours apart, at least 7 hours apart, at least 8 hours apart, at least 9 hours apart, at least 10 hours apart, at least 11 hours apart, at least 12 hours apart, at least 13 hours apart, at least 14 hours apart, at least 15 hours apart, at least 16 hours apart, at least 17 hours apart, at least 18 hours apart, at least 19 hours apart, at least 20 hours apart, at least 21 hours apart, at least 22 hours apart, at least 23 hours apart, or at least 24 hours apart.

According to some embodiments, pharmaceutical compositions are administered in a manner appropriate to the condition to be treated. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. The optimal dose depends upon the condition, body mass, weight, or blood volume of the patient.

According to some embodiments, the isoquinoline derivative is administered in an amount sufficient to treat disturbed cerebral homeostasis or any component thereof.

According to some embodiments, the isoquinoline derivative is administered in an amount sufficient to improve patient outcome, to improve neurological outcome, or to prevent ischemic neurological deficits in a subject, as compared with the outcome in the subject prior to administration or in a patient treated with placebo. According to some embodiments, the isoquinoline derivative is administered in an amount sufficient to improve a subject's outcome at least 1 point on any qualitative outcome measure relative to that of the subject prior to administration or of one or more patients on placebo. According to some embodiments, said improvement occurs within 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 30 days, 60 days, 90 days, 4 months, 5 months, 6 months, 7 months, 8 months, 9 months, 10 months, 11 months, 12 months, 13 months, 14 months, 15 months, 16 months, 17 months, 18 months, 2 years, 3 years, 4 years, or 5 years, following administration. According to some embodiments, said improvement is observed at time of discharge.

According to some embodiments, the isoquinoline derivative is administered in an amount sufficient to reduce the occurrence of elevated intracranial pressure, low systolic blood pressure, low cerebral perfusion pressure, low blood tissue oxygen pressure, pathological values on CMD-derived parameters, new cerebral infarcts, seizures, cerebral infarction, low-density areas on computerized tomography (CT) imaging, hypersensitivity reaction, paralytic ileus, elevated liver enzymes, thrombocytopenia, cardiac rhythm disturbances, angina pectoris, myocardial infarction, or a combination thereof.

According to some embodiments, the isoquinoline derivative is administered in an amount sufficient to reduce the occurrence, duration, or severity of elevated intracranial pressure, defined as mean intracranial pressure over 15 minutes of >15 mmHg, >16 mmHg, >17 mmHg, >18 mmHg, >19 mmHg, >20 mmHg, >21 mmHg, >22 mmHg, >23 mmHg, >24 mmHg, >25 mmHg, >26 mmHg, >27 mmHg, >28 mmHg, >29 mmHg, >30 mmHg, >31 mmHg, >32 mmHg, >33 mmHg, >31 mmHg, >35 mmHg, >36 mmHg, >37 mmHg, >38 mmHg, >39 mmHg, or >40 mmHg.

According to some embodiments, the isoquinoline derivative is administered in an amount sufficient to reduce the occurrence of elevated pulsatile intracranial pressure, defined as pulsatile intracranial pressure over 15 minutes of >2 mmHg, >3 mmHg, >4 mmHg, >5 mmHg, >6 mmHg, >7 mmHg, >8 mmHg, >9 mmHg, >10 mmHg, or more.

According to some embodiments, the isoquinoline derivative is administered in an amount sufficient to reduce the occurrence of Lundberg A waves or Lundberg B waves.

According to some embodiments, the isoquinoline derivative is administered in an amount sufficient to reduce the value of $PTD_{ICP30}$.

According to some embodiments, the isoquinoline derivative is administered in an amount sufficient to normalize cerebral perfusion pressure.

According to some embodiments, the isoquinoline derivative is administered in an amount sufficient to treat abnormal brain-tissue oxygen pressure.

According to some embodiments, the isoquinoline derivative is administered in an amount sufficient to treat pathological values of parameters derived from cerebral microdialysis.

According to some embodiments, administration of the isoquinoline derivative is initiated after a diagnostic finding of disturbed cerebral homeostasis. Such diagnostic findings include: detection of a hyperdense signal by a non-contrast CT scan in the basilar cisterns, sulci, ventricles and/or subarachnoid space; disclosure by a lumbar puncture of a raised red-blood-cell count (e.g. >2000×$10^6$ cells/L) or the presence of xanthochromia (by visual inspection or otherwise) in the cerebrospinal fluid; or confirmation by CT angiography of a vascular abnormality in the presence of a subarachnoid hemorrhage. According to some embodiments, said administration is initiated within one hour, within two hours, within three hours, within four hours, within five hours, within six hours, within seven hours, within eight hours, within nine hours, within ten hours, within eleven hours, within twelve hours, within thirteen hours, within fourteen hours, within fifteen hours, within sixteen hours, within seventeen hours, within eighteen hours, within nineteen hours, within twenty hours, within twenty-one hours, within twenty-two hours, within twenty-three hours, within a day, within two days, within three days, within four days, within five days, within six days, or within seven days, after the diagnostic finding.

According to some embodiments, the isoquinoline derivative is administered before, during or after a procedure to repair or secure an aneurysm, arteriovenous malformation, or other diseased blood vessel causing subarachnoid hemorrhage.

According to some embodiments, the isoquinoline derivative is administered before, during or after either a surgical, endovascular, or other procedure to mitigate the effects of a blood clot from a ruptured blood vessel causing intracerebral hemorrhage. According to some embodiments, the isoquinoline derivative is administered before, during or after either a surgical, endovascular, or other procedure to repair or secure an aneurysm.

According to some embodiments, the isoquinoline derivative is administered before, during or after administering another agent to reduce damaging effects of intracerebral hemorrhage. According to some embodiments, the isoquinoline derivative is administered before, during or after treatment with other drugs for the treatment of hemorrhages affecting the central nervous system.

According to some embodiments, the isoquinoline derivative is administered in conjunction with reperfusion therapy.

According to some embodiments, the isoquinoline derivative treats a damaging effect of ischemia or hemorrhage on the central nervous system.

According to some embodiments, the isoquinoline derivative treats abnormal ICP or a damaging effect of abnormal ICP in a subject or population of subjects. According to some embodiments, said treatment comprises: administering an isoquinoline derivative to subjects having a subarachnoid hemorrhage, wherein the damaging effect is reduced in the administered population compared to control subjects not receiving the isoquinoline derivative. The damaging effect that is reduced can be neuronal cell death or a cognitive deficit.

According to some embodiments, the isoquinoline derivative treats hydrocephalus or a damaging effect of hydrocephalus in a subject or population of subjects. According to some embodiments, said treatment comprises: administering an isoquinoline derivative to subjects having a subarachnoid hemorrhage, wherein the damaging effect is reduced in the administered population compared to control subjects not receiving the agent. The damaging effect that is reduced can be neuronal cell death or a cognitive deficit.

According to some embodiments, the isoquinoline derivative reduces neuronal damage, reduces the area of hypoperfusion, reduces cortical spreading depolarization, reduces cortical spreading depression, treats ischemic stroke before definitive diagnosis thereof, inhibits development of neurocognitive deficits in the subject, reduces a damaging effect of abnormal ICP in or otherwise affecting the CNS of a subject, reduces pain in the subject from surgery to remediate ischemia or hemorrhage, reduces pain resulting from endovascular surgery, reduces pain along a path traversed by an endoscope used in performing the endoscopic surgery, reduces low-density areas on computerized tomography imaging, inhibits development of infarcts in the CNS detectable by CT or MRI, or inhibits development of infarctions detectable by CT or MRI.

According to some embodiments, the isoquinoline derivative is administered orally, intrathecally, intravenously, intra-arterially, intra-peritoneally, parenterally, or through inhalation.

According to some embodiments, intra-arterial administration is performed at the femoral artery.

According to some embodiments, treatment of disturbed cerebral homeostasis includes the prevention of neurological deficits, improvement of patient outcome, improvement of qualitative outcome measures, improvement of neurological outcome, or reduction in the incidence or severity of ischemic deficits.

According to some embodiments, neurological outcome is assessed by: laboratory tests; analysis of concomitant medications; physical examinations; mental evaluations; physical evaluations; electrocardiograms (ECGs); vital signs; radiographic assessments; assessments of impulse control; changes in disease symptoms; Mini Mental State Examination; examinations using the Jay Midi Scale; UDysRS; Hoehn and Yahr scale; Clinical Global impression scale; Patient global impression scale; Lang-Fahn daily activity scale; the frequency and/or intensity of adverse events; infarction volume (i.e., the volume of dead neuronal cells in the brain); the number of ischemic lesions; the number of infarctions and the location of the infarction(s) in the brain; any qualitative or quantitative measures of improvement to disturbed cerebral homeostasis or any component thereof; reductions in neurological deficits; changes (including improvements) in neurological outcome; reductions in the incidence or severity of ischemic deficits; reductions in all-cause mortality or vasospasm-related mortality; changes (including improvements) in any qualitative or quantitative measure; reductions in the occurrence, duration, or severity of elevated intracranial pressure, low systolic blood pressure, abnormal cerebral perfusion pressure, abnormal blood tissue oxygen pressure, pathological values on CMD-derived parameters, new cerebral infarcts, seizures, cerebral infarction, low-density areas on computerized tomography (CT) imaging, hypersensitivity reaction, paralytic ileus, elevated liver enzymes, thrombocytopenia, cardiac rhythm disturbances, angina pectoris, myocardial infarction, elevated pulsatile intracranial pressure, abnormal pulsatile ICP waveforms, Lundberg A waves, Lundberg B waves, $PTD_{ICP30}$ value, early brain injury, delayed cerebral ischemia (DCI), delayed ischemic neurological deficit, or a combination thereof; or any combination of any of the foregoing. Laboratory tests include, but are not limited to, urine analysis, serum cotinine analysis, urine cotinine analysis, serum nicotine analysis, hematology, chemistry, and pregnancy. Adverse events include, but are not limited to, nausea, dizziness, constipation, hypotension, vomiting, fatigue, pain, diarrhea, headache, pain in extremity, tremor, nightmare, or insomnia.

According to some embodiments, neurological outcome is assessed by the presence of symptoms, such as fatigue, mood disturbances, depression, executive dysfunction, anxiety, depression, posttraumatic stress disorder, cognitive impairment, headaches, hormonal dysregulation, irregular hormone production, and deficiencies in one or more of the hypothalamic-pituitary hormones (including but not limited to growth hormone, prolactin or thyroid-stimulating hormone).

According to some embodiments, neurological outcome is assessed by restoration of cerebral metabolism (e.g., as measured by jugular bulb oxygen saturation); intracerebral microdialysis measurements of lactate, pyruvate and glutamate; brain tissue oxygen; or a combination thereof, as compared to a control. According to some embodiments, neurological outcome is assessed by a restoration of the integrity of the blood brain barrier or a reduction in the need for rescue therapy.

According to some embodiments, neurological outcome is assessed by the presence of cerebral infarction, as detected by CT or MM scan of the brain within 6 weeks after treatment, not present on the CT or MM scan between 24 and 48 hours after treatment, and not attributable to other causes such as surgical clipping or endovascular treatment.

According to some embodiments, patient outcome (e.g., neurological outcome) is assessed about 30 days, 60 days, 90 days, 180 days, 3 months, 6 months, 9 months, or 12 months post-ictus.

According to some embodiments, patient outcome (e.g., neurological outcome) is assessed about 30 days, 60 days, 90 days, 180 days, 3 months, 6 months, 9 months, or 12 months post-treatment.

According to some embodiments, patient outcome (e.g., neurological outcome) is assessed about 30 days, 60 days, 90 days, 180 days, 3 months, 6 months, 9 months, or 12 months post-discharge.

According to some embodiments, patient outcome (e.g., neurological outcome) is assessed by reference to condition while in-hospital. According to some embodiments, patient outcome (e.g., neurological outcome) is assessed at time of discharge.

According to some embodiments, the subject's score on the Barthel Index improves after treatment. According to some embodiments, the improvement is an increase in the subject's Barthel Index score by an integer between 1 and 99.

According to some embodiments, the subject's score on the conventional Glasgow Outcome Scale improves after treatment. According to some embodiments, the improvement is a change in the Glasgow Outcome Scale from 1 to 2; from 1 to 3; from 1 to 4; from 1 to 5; from 2 to 3; from 2 to 4; from 2 to 5; from 3 to 4; from 3 to 5; or from 4 to 5.

In certain embodiments, the subject's score on the Glasgow Outcome Scale—Extended improves after treatment. According to some embodiments, the improvement is a change in the Glasgow Outcome Scale—Extended from 2 to 3; from 2 to 4; from 2 to 5; from 2 to 6; from 2 to 7; from 2 to 8; from 3 to 4; from 3 to 5; from 3 to 6; from 3 to 7; from 3 to 8; from 4 to 5; from 4 to 6; from 4 to 7; from 4 to 8; from 5 to 6; from 5 to 7; from 5 to 8; from 6 to 7; from 6 to 8; or from 7 to 8.

According to some embodiments, the subject's score on the modified Rankin Scale improves after treatment. According to some embodiments, the improvement is a change in the subject's score on the modified Rankin Scale from 5 to 4; from 5 to 3; from 5 to 2; from 5 to 1; from 5 to 0; from 4 to 3; from 4 to 2; from 4 to 1; from 4 to 0; from 3 to 2; from 3 to 1; from 3 to 0; from 2 to 1; from 2 to 0; or from 1 to 0.

According to some embodiments, patient outcome improves following treatment. According to some embodiments, the improvement is a less detectable focal contrast enhancement in the subject's leptomeningeal compartment when imaged by a 3-tesla (postcontrast or non-contrast) T2-weighted, fluid-attenuated inversion recovery (FLAIR) MRI; a less detectable postcontrast or non-contrast T2 signal hyperintensity in the leptomeningeal compartment, the parenchyma or the intracranial vasculature; a reduction of the subject's erythrocyte sedimentation rate (ESR); a reduction of the subject's serum C-reactive protein concentration;

a reduction of an adult subject's opening pressure in response to a lumbar puncture performed in the lateral decubitus position with the legs and neck in a neutral position; a reduction of the subject's cerebrospinal fluid protein as measured in mg/dL; a reduction of the subject's cerebrospinal fluid protein as measured in mg % by an early lumbar tap relative to ictus; a reduction of the subject's cerebrospinal fluid protein as measured in mg % by a late lumbar tap relative to ictus; a reduction the subject's leukocyte count; or a reduction of the subject's percentage of polymorphonuclear cells.=

According to some embodiments, the subject's abnormal ICP improves following treatment. According to some embodiments, the improvement is a reduction of mean ICP in: an adult with or at risk of a mean ICP above 5 mmHg; a child with or at risk of a mean ICP above 3 mmHg; or an infant with or at risk of a mean ICP above 1.5 mmHg. According to some embodiments, the improvement is a restoration to the normal ICP waveform in a subject with, or at risk of a rounded or abnormal ICP waveform. According to some embodiments, the improvement is a reduction of ICP waveform amplitude in a subject with or at risk of an ICP waveform greater than 4 mmHg in amplitude. According to some embodiments, the improvement is a reduction of ICP waveform in a subject with or at risk of an ICP waveform more than 30% of the mean ICP. According to some embodiments, the improvement is a reduction of P2 in a subject with or at risk of an ICP waveform in which P2 is greater than P1. According to some embodiments, the improvement is: a reduction of ICP waveform peaks (dP) in a subject with or at risk of large-amplitude ICP waveform peaks (dP); a lengthening of ICP waveform rise times (dT) in a subject with or at risk of shortened ICP waveform rise times (dT); or a decrease in ICP rise time coefficients (dP/dT) in a subject with or at risk of increased ICP rise time coefficients (dP/dT). According to some embodiments, the improvement is a reduction in frequency, duration or intensity of Lundberg A waves in a subject with or at risk of Lundberg A waves. According to some embodiments, the improvement is a reduction in frequency, duration or intensity of Lundberg B waves in a subject with or at risk of Lundberg B waves. According to some embodiments, the improvement is a reduction in pulsatile ICP in a subject with or at risk of a pulsatile ICP greater than 5 mmHg. According to some embodiments, the improvement is a reduction in $PTD_{ICP30}$ in a subject with or at risk of a $PTD_{ICP30}$ greater than 1.

According to some embodiments, administration of the isoquinoline derivative does not reduce systemic blood pressure. According to some embodiments, administration of the isoquinoline derivative does not reduce systolic or diastolic pressure by more than 5%, 10%, 15%, 20%, 25%, 30%, 35%, 40%, 45%, 50%, 60%, or 70%. According to some embodiments, administration of the isoquinoline derivative does not reduce systemic blood pressure (or systolic or diastolic pressure alone) for more than 5 minutes, for more than 10 minutes, for more than 15 minutes, for more than 20 minutes, for more than 30 minutes, for more than 45 minutes, for more than 60 minutes, for more than 75 minutes, for more than 90 minutes, for more than 105 minutes, or for more than 120 minutes.

According to some embodiments, provided herein are kits, wherein the kits may comprise pharmaceutical compositions comprising a isoquinoline derivative. According to some embodiments, the isoquinoline derivative is belumosudil, hydroxyfasudil, dimethylfasudil, fasudil, netarsudil, or ripasudil, or a salt thereof.

According to some embodiments, the kits comprise an isoquinoline derivative or a salt thereof. The kits may be used for treating disturbed cerebral homeostasis (including elevated intracranial pressure) in a subject. The kits may be used for improving cognitive-related symptoms or motor-related symptoms in a subject. The kits may be used for reducing neurological deficits following elevated intracranial pressure. The kits may be used for improving neurological outcome following elevated intracranial pressure.

According to some embodiments, the kits may provide a total dose of isoquinoline derivative or a salt thereof per day. According to some embodiments, the total dose of isoquinoline derivative or the salt thereof may be more than 24 mg per day. The total dose of isoquinoline derivative or a salt thereof may be no more than about 4 mg per day, 6 mg per day, 8 mg per day, 10 mg per day, 12 mg per day, 14 mg per day, 16 mg per day, 18 mg per day, 20 mg per day, 22 mg per day, 24 mg per day, 26 mg per day, 28 mg per day, 30 mg per day, 32 mg per day, 34 mg per day, 36 mg per day, 38 mg per day, 40 mg per day, 42 mg per day, 44 mg per day, 46 mg per day, 48 mg per day, or more than 48 mg per day. The total dose of isoquinoline derivative or a salt thereof may be in a range of about 1 mg per day to 24 mg per day, 2 mg per day to 22 mg per day, 3 mg per day to 20 mg per day, 4 mg per day to 18 mg per day, 5 mg per day to 16 mg per day, 6 mg per day to 14 mg per day, or 8 mg per day to 12 mg per day. The total dose of isoquinoline derivative or a salt thereof may be in a range of about 8 mg per day to 24 mg per day. The kits may provide a dose of isoquinoline derivative or a salt thereof over the period of time for administration at least once a day.

According to some embodiments, the kits may provide a dose of isoquinoline derivative or a salt thereof over a period of time. The kits may provide a plurality of doses. The kits may provide 1, 2, 3, 4, 5, 6, 7, 8, 9, or 10 different doses of the isoquinoline derivative or salt thereof.

According to some embodiments, the kits may provide a dose of isoquinoline derivative or a salt thereof over a period of time, wherein the dose can be escalated upward at treatment intervals. The kits may provide a plurality of doses. The kits may provide 1, 2, 3, 4, 5, 6, 7, 8, 9, or 10 different doses of the isoquinoline derivative or salt thereof. The dose of the isoquinoline derivative or salt thereof may be about 1 mg, 2 mg, 3 mg, 4 mg, 5 mg, 10 mg, 15 mg, 20 mg, 30 mg, 40 mg, 45 mg, 50 mg, 60 mg, 120 mg, 150 mg, 180 mg, or more than 240 mg. The dose may be about 1 mg, 2 mg, 3 mg, 4 mg, 5 mg, 10 mg, 15 mg, 20 mg, 30 mg, 40 mg, 45 mg, 50 mg, 60 mg, 120 mg, 150 mg, 180 mg or more than 240 mg. The dose may be at least or about 1 mg, 2 mg, 3 mg, 4 mg, 5 mg, 10 mg, 15 mg, 20 mg, 30 mg, 40 mg, 45 mg, 50 mg, 60 mg, 120 mg, 150 mg, 180 mg, or more than 240 mg. The dose may be about 1 mg, 2 mg, 3 mg, 4 mg, 5 mg, 10 mg, 15 mg, 20 mg, 30 mg, 40 mg, 45 mg, 50 mg, 60 mg, 120 mg, 150 mg, 180 mg or more than 240 mg. The period of time may be 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, or more than 12 weeks. The kits may provide a dose of isoquinoline derivative or a salt thereof over the period of time for administration at least once a day. Administration may be 1, 2, 3, 4, 5, 6, 7, 8, 9, 10, 11, 12 more than 12 times a day. Administration may be every 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. The dose may be escalated upward at two weeks treatment intervals. The dose may be escalated upward at 1 week to 4 week treatment intervals. The dose may be escalated upward at 1-day, 2-day, 3-day, 4-day, 5-day, 6-day, 1-week, 2-week, 3-week, 4-week, 5-week, 6-week, 7-week, 8-week, or more than 8-week treatment intervals. The kits may provide for a plurality of escalated doses from a starting dose. The kits may provide for a plurality of different or non-identical escalated doses from a starting dose.

According to some embodiments, provided herein are kits comprising a total dosage of isoquinoline derivative or salt thereof. According to some embodiments, the total dosage of the isoquinoline derivative or salt thereof is for a period of time. The total dosage may be about 5 mg, 7 mg, 10 mg, 15 mg, 20 mg, 2 mg, 30 mg, 35 mg, 40 mg, 45 mg, 50 mg, 60 mg, 70 mg, 80 mg, 90 mg, 100 mg, 120 mg, 140 mg, 160 mg, 180 mg, 200 mg, 225 mg, 250 mg, 275 mg 300 mg, 350 mg, 400 mg, 450 mg, 500 mg, 550 mg, 600 mg, 650 mg, 700 mg, 750 mg, 800 mg, or more than 800 mg of the isoquinoline derivative or salt thereof. The period of time may be 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, or more than 12 weeks. The kits may provide for administration of the isoquinoline derivative or salt thereof at least once a day. Administration may be 1, 2, 3, 4, 5, 6, 7, 8, 9, 10, 11, 12 more than 12 times a day. Administration may be every 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. For example, for 6 mg dose of isoquinoline derivative or salt thereof for 4 weeks and administration 4 times a day, the kit provides a total dosage of the isoquinoline derivative or salt thereof of 672 mg.

According to some embodiments, the kits may provide a dose of isoquinoline derivative or a salt thereof that can be administered at least once a day. The dose of isoquinoline derivative or a salt thereof may be administered at least 1, 2, 3, 4, 5, 6, 7, 8, 9, 10, 11, 12, or more than 12 times a day. The dose of isoquinoline derivative or a salt thereof may be administered about 1, 2, 3, 4, 5, or 6 times a day. The dose of isoquinoline derivative or a salt thereof may be administered once a day. The dose of isoquinoline derivative or a salt thereof may be administered twice a day. A time between administration may be at least 1 hour, 2 hours, 3 hours, 4 hours, 5 hours, 6 hours, 7 hours, 8 hours, 9 hours, 10 hours, 11 hours, 12 hours, or more than 12 hours. A time between administration may be in a range of 0 hours to 24 hours, 1 hour to 23 hours, 2 hours to 22 hours, 3 hours to 21 hours, 4 hours to 20 hours, 5 hours to 19 hours, 6 hours to 18 hours, 7 hours to 17 hours, 8 hours to 16 hours, 9 hours to 15 hours, and 10 hours to 12 hours. A time between administration may be in a range of about 1 hour to about 6 hours or about 2 hours to about 6 hours. Administration may be every 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours.

According to some embodiments, the kits may provide a dosage form that delivers an immediate-release dose of the isoquinoline derivative or the salt thereof followed by a second-immediate release dose about 2 hours to 8 hours after administration. The dosage form may deliver an immediate-release dose of the isoquinoline derivative or the salt thereof followed by a second-immediate release dose about 1 hour to 8 hours, 1 hour to 7 hours, 1 hour to 6 hours, 1 hour to 5 hours, 1 hour to 4 hours, 1 hour to 3 hours, 2 hours to 8 hours, 2 hours to 7 hours, 2 hours to 6 hours, 2 hours to 5 hours, or 2 hours to 4 hours after administration. According to some embodiments, the second-immediate release dose is followed by a third-immediate release dose about 8 hours to about 16 hours after administration. According to some embodiments, the third-immediate release dose is followed by a fourth-immediate release dose about 16 hours to about 24 hours after administration. The dose of isoquinoline derivative or the salt thereof may be about 1 mg to about 6 mg over a period of time. For example, the dose of isoquinoline derivative or the salt thereof may be about 1 mg to about 6 mg over 6 hours. The dose may comprise at least or about 1 mg, 2 mg, 3 mg, 4 mg, 5 mg, 6 mg, 7 mg, 8 mg, 9 mg, 10 mg, 11 mg, 12 mg, or more than 12 mg of isoquinoline derivative or a salt thereof. The dose may comprise at least or about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 26 mg, 28 mg, 30 mg, 32 mg, 34 mg, 36 mg, 38 mg, 40 mg, 42 mg, 44 mg, 46 mg, 48 mg, or more than 48 mg of isoquinoline derivative or a salt thereof. The period of time may be 1 hour, 2 hours, 3 hours, 4 hours, 5 hours, 6 hours, 7 hours, 8 hours, 9 hours, 10 hours, 11 hours, 12 hours, or more than 12 hours. The dose of isoquinoline derivative or a salt thereof may be administered at least 1, 2, 3, 4, 5, 6, 7, 8, 9, 10, 11, 12, or more than 12 times a day. The dose of isoquinoline derivative or a salt thereof may be administered about 1, 2, 3, 4, 5, or 6 times a day. The dose of isoquinoline derivative or a salt thereof may be administered once a day. The dose of isoquinoline derivative or a salt thereof may be administered twice a day. A time between administration may be at least or within a range spanning 1 hour, 2 hours, 3 hours, 4 hours, 5 hours, 6 hours, 7 hours, 8 hours, 9 hours, 10 hours, 11 hours, 12 hours, more than 12 hours, or more than 12 hours. A time between administration may be in a range of 0 hours to 24 hours, 1 hour to 23 hours, 2 hours to 22 hours, 3 hours to 21 hours, 4 hours to 20 hours, 5 hours to 19 hours, 6 hours to 18 hours, 7 hours to 17 hours, 8 hours to 16 hours, 9 hours to 15 hours, and 10 hours to 12 hours.

According to some embodiments, the kits provide a dosage form of isoquinoline derivative or salt thereof that delivers one or more immediate-release doses of the isoquinoline derivative or the salt thereof over a period of time. A number of immediate-release doses of the isoquinoline derivative or the salt thereof may be 1, 2, 3, 5, 6, 7, 8, or more than 8 immediate-release doses. A number of immediate-release doses of the isoquinoline derivative or salt thereof may be in a range of 1 to 8, 1 to 7, 1 to 6, 1 to 5, 1 to 4, 1 to 3, 2 to 8, 2 to 7, 2 to 6, 2 to 5, 2 to 4 immediate-release doses. The dosage form may provide an immediate-release dose about 1 hour to 8 hours, 1 hour to 7 hours, 1 hour to 6 hours, 1 hour to 5 hours, 1 hour to 4 hours, 1 hour to 3 hours, 2 hours to 8 hours, 2 hours to 7 hours, 2 hours to 6 hours, 2 hours to 5 hours, or 2 hours to 4 hours after administration. The dosage form may provide an immediate-release dose about 8 hours to 16 hours, 8 hours to 15 hours, 8 hours to 14 hours, or 8 hours to 12 hours after administration. The dosage form may provide an immediate-release dose about 16 hours to 24 hours, 16 hours to 22 hours, 16 hours to 20 hours, or 16 hours to 18 hours after administration.

According to some embodiments, the kits may provide a dosage form that delivers a delayed-release pulse of the isoquinoline derivative or the salt thereof. The delayed-release pulse of the isoquinoline derivative or the salt thereof may be delivered over a period of time. A dose of isoquinoline derivative or the salt thereof may be no more than 24 mg per day. According to some embodiments, the dose of isoquinoline derivative or the salt thereof may be more than 24 mg per day. The dose may comprise at least or about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, or more than 24 mg of isoquinoline derivative or a salt thereof. The dose may comprise at least or about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 26 mg, 28 mg, 30 mg, 32 mg, 34 mg, 36 mg, 38 mg, 40 mg, 42 mg, 44 mg, 46 mg, 48 mg, or more than 48 mg of isoquinoline derivative or a salt thereof. The period of time may be or within a range spanning 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or more than 24 hours.

According to some embodiments, provided herein are kits that may be used for chronic treatment. The treatment period may be more than 12 weeks. The treatment period may be 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, or more than 8 years.

According to some embodiments, the kits may contain a dose of isoquinoline derivative or a salt thereof provided as a unit dose. The kits may comprise one or more unit doses. The one or more unit doses may comprise about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, or more than 24 mg of isoquinoline derivative or a salt thereof. The one or more unit doses may comprise at least or at most 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, or more than 24 mg of isoquinoline derivative or a salt thereof. The kits may comprise 1, 2, 4, 6, 8, 10, 12, 14, 16, 18, 20, 24, 26, 28, 30, 35, 40, 45, 50, or more than 50 unit doses. The kits may comprise one or more unit doses of different doses of the isoquinoline derivative or salt thereof. A number of different or non-identical doses may include, but is not limited, 1, 2, 3, 5, 6, 7, 8, 9, 10, 11, 12 or more than 12 different or non-identical doses of the isoquinoline derivative or salt thereof. The one or more unit doses may be formulated for oral, intravenous, intraarterial, parenteral, buccal, topical, transdermal, rectal, intramuscular, subcutaneous, intraosseous, transmucosal, or intraperitoneal administration. The one or more unit doses may be formulated for oral, topical, buccal, transdermal, or inhalation administration. The one or more unit doses may be formulated for oral administration. The one or more unit doses may be formulated as a liquid, gel, semi-liquid, semi-solid, or solid form. The one or more unit doses may be formulated as a capsule, cachet, tablet, liquid, or aerosol spray. The one or more unit doses may be formulated as a tablet. The one or more unit doses may be formulated as a capsule. The one or more unit doses may be formulated as a food. The one or more unit doses may be formulated as a beverage. The one or more unit doses may be formulated as a dietary supplement.

According to some embodiments, the kits may further comprise instructions for use of the kit according to the various methods and approaches described herein. The instructions may be related to use of a composition as described herein. The instructions may be related to use of isoquinoline derivative or a salt thereof. For example, the instructions relate to a total dose per day, total dosage over a period of time, amount of time between administration, number of times a day for administration, dose amount at each time of administration, dose escalation, treatment intervals, evaluative measurements to be taken, or combinations thereof. The instructions may relate to evaluation of the subject by a physician. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer. Kits may also comprise an aid to administration of the active agent formulation, such as an inhaler, spray dispenser (e.g., nasal spray), syringe for injection or pressure pack for capsules, tablets, or suppositories.

Example 1

A sharpened 4-0 nylon suture was introduced into the left internal carotid artery of 92 adult male Sprague-Dawley rats weighing 260-340 mg. In 65 of the 92 rats, the bifurcation of the anterior and middle cerebral arteries was endovascularly perforated; in the remaining 27 rats, the suture was withdrawn without perforation.

At 0.5 hours after the procedure, 34 of the 65 perforated rats were administered 1.5 ml of 0.9% saline (vehicle group), and the remaining 31 were administered 10 mg/kg hydroxyfasudil dissolved in 1.5 ml of 0.9% saline (hydroxyfasudil group). The 27 unperforated rats received neither vehicle nor saline (sham group).

24 hours after the procedure, all rats were sacrificed. The animals' brains were removed and separated into left hemisphere, right hemisphere, cerebellum and brain stem. Each part was weighed immediately after removal (wet weight) and after drying in 100° C. for 72 h (dry weight). The percentage of water content was calculated as [(wet weight−dry weight)/wet weight]×100%. The results are shown in Tables 1 and 2.

In the left hemisphere, the percentage of water content was approximately 79.0% in the sham group; 79.7% in the vehicle group; and 79.3% in the hydroxyfasudil group. Perforation therefore resulted approximately in a 0.7% increase in water content in the left hemisphere between the sham group and the vehicle group. Treatment with hydroxyfasudil reduced the increase to about 0.3%, showing an improvement of about 57% ($p<0.01$) in the left hemisphere.

In the right hemisphere, the percentage of water content was approximately 79.1% in the sham group; 79.6% in the vehicle group; and 79.25% in the hydroxyfasudil group. Perforation therefore resulted approximately in a 0.5% increase water content in the right hemisphere between the sham group and the vehicle group. Treatment with hydroxyfasudil reduced the increase to about 0.25%, showing an improvement of about 70% ($p<0.01$) in the right hemisphere.

In the cerebellum, the percentage of water content was approximately 78.5% in the sham group; 79.1% in the vehicle group; and 78.7% in the hydroxyfasudil group. Perforation therefore resulted approximately in a 0.6% increase in water content in the cerebellum between the sham group and the vehicle group. Treatment with hydroxyfasudil reduced the increase to about 0.2%, showing an improvement of about 67% ($p<0.05$) in the cerebellum.

TABLE 1

Mean percentage of brain water content following one treatment at 24 hrs post-surgery (approximated from Fujii 2012)

| | Treatment | | | p-value |
|---|---|---|---|---|
| | Sham (n = 27) | Vehicle (n = 34) | HF (n = 31) | (HF v. vehicle) |
| Left Hemisphere | 79.05% | 79.7% | 79.3% | <0.01 |
| Right Hemisphere | 79.2% | 79.65% | 79.35% | <0.01 |
| Cerebellum | 78.55% | 79.2% | 78.7% | <0.05 |

TABLE 2

Mean percentage of brain water content following two treatments at 24 hrs post-surgery (approximated from Fujii 2012)

| | Treatment | | | p-value |
|---|---|---|---|---|
| | Sham | Vehicle (n = 9) | HF (n = 11) | (HF v. vehicle) |
| Left Hemisphere | 79.05% | 79.6% | 79.3% | <0.01 |
| Right Hemisphere | 79.2% | 79.5% | 79.25% | <0.01 |
| Cerebellum | 78.55% | 79.1% | 78.84% | N.S. |

However, concurrent experiments involving two treatments instead of one, and measurements taken at 72 hours after perforation instead of 24 hours, failed to demonstrate any significant differences in brain water content or neurological performance between the vehicle group and hydroxyfasudil group. (Fujii et al. (2012)).

It is inferred from this raw data that hydroxyfasudil (and its prodrug fasudil) mediates intracranial fluid dynamics in a manner that can treat disturbed homeostasis, and in particular, abnormal ICP or hydrocephalus.

Example 2

The same rats from Example 1 were evaluated prior to sacrifice for neurologic performance 24 hours after the endovascular perforation. Neurological scores on six tests (spontaneous activity, symmetrical limb movements, forelimb outstretching, climbing a wall of a wire cage, axillary touch response, and vibrissae touch response) were assessed using a modified Garcia scoring system (Garcia et al., 1995; Sugawara et al., 2008). The neurological score was significantly lower in the vehicle group (mean score of 10 out of 18) compared to the hydroxyfasudil group (mean score of 14 out of 18) ($p<0.05$). (Fujii et al. (2012)). The results are shown in Table 3.

TABLE 3

Garcia neurological score (approximated from Fujii 2012)

| Number of Treatments | Hrs. post treatment | Treatment | | | p-value |
|---|---|---|---|---|---|
| | | Sham | SAH + Vehicle | SAH + HF | (HF v. vehicle) |
| 1 | 24 | 16 | 10 | 14 | <0.05 |
| 2 | 24 | 16 | 13 | 15.5 | N.S. |
| 1 | 72 | 17 | 13.5 | 14 | N.S. |

It is inferred from this raw data that fasudil mediates intracranial fluid dynamics in a manner that can improve patient outcomes (including neurologic performance) following disturbed homeostasis, and in particular, abnormal ICP or hydrocephalus.

Example 3

Following the general framework of the INTERACT-2 protocol, a randomized, placebo-controlled trial will include patients, residing in North America or any one or more of the States within the European Community, who are adjudged to be at risk of disturbed cerebral homeostasis with computed tomographic-confirmed spontaneous ICH within 6 hours of onset and elevated systolic blood pressure (systolic BP, 150-220 mmHg).

The study protocol will be approved by all relevant regulatory authorities and local institutional review boards. The study will be completed in accordance with Good Clinical Practice guidelines and the Declaration of Helsinki. All patients participating in the study must first give informed consent.

Upon confirmation of eligibility, stroke severity will be measured using the Glasgow Outcome Scale and National Institutes of Health Stroke Scale at baseline, 24 hours, and at day 7 (or earlier on discharge from hospital). Uncompressed digital images of all baseline and follow-up CT scans will be collected in DICOM format, identified only with the patient's unique study number, for central analysis of ICH and IVH volumes blind to clinical data, treatment, and date and sequence of scan, using computer-assisted multislice planimetric and voxel threshold techniques. Inter-reader reliability will be checked by periodic reanalysis of 15% of the scans reviewed by each imaging scientist against a single neurologist to avoid drift.

Subjects will be administered 30 mg intravenous fasudil hydrochloride twice or three times per day, for up to 14 consecutive days.

Patient outcome measures may include one or more of the following: qualitative, quantitative or functional measures of improvement to disturbed cerebral homeostasis or any component thereof; changes (including improvements) in neurological outcome or presence of ischemic neurological deficits in a subject, as compared with the outcome in a patient treated with placebo; changes (including improvements) on any qualitative, quantitative or functional outcome measure; changes (including reductions) in the occurrence, duration, or severity of elevated intracranial pressure, low systolic blood pressure, abnormal cerebral perfusion pressure, abnormal blood tissue oxygen pressure, pathological values on CMD-derived parameters, new cerebral infarcts, seizures, cerebral infarction, low-density areas on computerized tomography (CT) imaging, hypersensitivity reaction, paralytic ileus, elevated liver enzymes, thrombocytopenia, cardiac rhythm disturbances, angina pectoris, myocardial infarction, elevated pulsatile intracranial pressure, Lundberg A waves, Lundberg B waves, $PTD_{ICP30}$ value, Lawton Instrumental Activities of Daily Living Scale score, or a combination thereof. Patient outcome in this prophetic example will be assessed at 30 days, 90 days, and 6 months.

Example 4

A randomized, placebo-controlled trial will include individuals residing in North America or the European Community, and between 18-75 years in age, who are diagnosed with abnormal ICP or hydrocephalus following visualization of a diffuse clot (long axis≥20 mm or present in both hemispheres) on an admission CT scan and diagnosis of a World Federation of Neurological Surgeons (WFNS) grade I-IV subarachnoid hemorrhage due to ruptured saccular aneurysm. The trial will exclude patients with subarachnoid hemorrhage due to non-aneurysmal causes, intraventricular or intracerebral hemorrhage without subarachnoid blood, angiographic vasospasm on admission angiography, or major complications during the securing procedure.

The study protocol will be approved by all relevant regulatory authorities and local institutional review boards. The study will be completed in accordance with Good Clinical Practice guidelines and the Declaration of Helsinki. All patients participating in the study must first give informed consent.

Immediately upon confirmation of eligibility, all consenting patients will be given standard of care (including but not limited to oral nimodipine). Patients for whom nimodipine is deemed inappropriate or suboptimal will be randomized to receive either fasudil or placebo. Patients randomized to fasudil will be administered 30 mg fasudil hydrochloride by intravenous infusion 2-3 times each day for up to 14 days after the aSAH. Patients randomized to receive placebo will receive saline by intravenous infusion 2-3 times each day for up to 14 days after the aSAH. Intracranial pressure, hydrocephalus and neuroinflammatory markers will be evaluated at regular intervals or upon appearance of irregularities.

Sites will manage patients according to guidelines developed for the study that are consistent with published recommendations. These guidelines include recommendations for maintaining or increasing blood pressure by preferentially using vasopressors and limiting the administration of fluids. Early detection and management of lung complications must also be addressed. Drugs or procedures not considered to be standard care will be prohibited.

Patient outcome measures in this prophetic example may include any described in Example 3 above.

Example 5

In an adult patient with an ICP>20 mmHg and suspected bacterial meningitis as determined by lumbar puncture, one would administer by intravenous infusion 60 mg fasudil hydrochloride. One would place an intraparenchymal device to measure ICP in the patient. One would envision intraparenchymal measurements would confirm reduction of ICP upon fasudil infusion in this prophetic example.

Other Embodiments

Fasudil, or a pharmaceutically acceptable salt thereof, for use in the prevention or treatment of increased intracranial pressure (ICP) in a subject, wherein the subject has suffered a brain injury that deposits blood in the subarachnoid space, and the subject is determined to be intolerant of nimodipine, wherein the treatment comprises administering to the subject fasudil or a pharmaceutically acceptable salt thereof.

Fasudil, or a pharmaceutically acceptable salt thereof, for use in the prevention or treatment of disturbed cerebral homeostasis in a subject, wherein the subject either has meningitis or has suffered a brain injury that deposits blood in the subarachnoid space; wherein the treatment comprises parenterally administering to said subject a therapeutic amount of fasudil, or a pharmaceutically acceptable salt thereof; and wherein said therapeutic amount is effective either to prevent neurological deficits or to improve neurological outcome or to reduce the incidence or severity of ischemic deficits.

Fasudil, or a pharmaceutically acceptable salt thereof, for use in the prevention or treatment of disturbed cerebral homeostasis in a subject, wherein the subject has suffered from meningitis or a brain injury that deposits blood in the subarachnoid space, wherein said subject is intolerant or determined to be intolerant of enteric nimodipine wherein said treatment comprises administering to said subject 30 mg of fasudil, or a pharmaceutically acceptable salt thereof, and detecting at 90 days an improvement in the Lawton Instrumental Activities of Daily Living Scale score.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of treating a patient experiencing disturbed cerebral homeostasis:
   wherein said disturbed cerebral homeostasis is selected from the group consisting of abnormal ICP, hydrocephalus, and acute CNS neuroinflammation;
   wherein said patient is determined to be intolerant of nimodipine;
   wherein said patient has developed dose-limiting hypotension in response to nimodipine; and
   wherein said method comprises administering to said patient an effective amount of fasudil hydrochloride.

2. A method of treating a patient experiencing disturbed cerebral homeostasis:
   wherein said patient has developed systolic blood pressure of less than 90 mmHg in response to nimodipine; and
   wherein said disturbed cerebral homeostasis is selected from the group consisting of abnormal ICP, hydrocephalus, and acute CNS neuroinflammation;
   wherein said method comprises administering to said patient an effective amount of fasudil hydrochloride.

3. The method of claim 1, wherein said disturbed cerebral homeostasis comprises a mean intracranial pressure above 5 mmHg.

4. The method of claim 2, wherein said disturbed cerebral homeostasis comprises a mean intracranial pressure above 5 mmHg.

5. The method of claim 1, wherein said disturbed cerebral homeostasis follows a brain injury that deposits blood in the subarachnoid space.

6. The method of claim 2, wherein said disturbed cerebral homeostasis follows a brain injury that deposits blood in the subarachnoid space.

7. The method of claim 3, wherein said disturbed cerebral homeostasis follows a brain injury that deposits blood in the subarachnoid space.

8. The method of claim 5, wherein said nimodipine was administered enterically.

9. The method of claim 6, wherein said nimodipine was administered enterically.

10. The method of claim 7, wherein said nimodipine was administered enterically.

\* \* \* \* \*